United States Patent
Panken et al.

(10) Patent No.: US 8,958,885 B2
(45) Date of Patent: Feb. 17, 2015

(54) POSTURE STATE CLASSIFICATION FOR A MEDICAL DEVICE

(75) Inventors: Eric J. Panken, Edina, MN (US); Dennis M. Skelton, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1521 days.

(21) Appl. No.: 12/433,004

(22) Filed: Apr. 30, 2009

(65) Prior Publication Data

US 2010/0010380 A1    Jan. 14, 2010

Related U.S. Application Data

(60) Provisional application No. 61/080,049, filed on Jul. 11, 2008.

(51) Int. Cl.
| | |
|---|---|
| *A61N 1/00* | (2006.01) |
| *A61N 1/365* | (2006.01) |
| *A61B 5/11* | (2006.01) |
| *A61B 5/00* | (2006.01) |

(52) U.S. Cl.
CPC .......... *A61N 1/36542* (2013.01); *A61B 5/1116* (2013.01); *A61B 5/1118* (2013.01); *A61B 5/7264* (2013.01); *A61B 2562/0219* (2013.01); *A61N 1/36535* (2013.01); *A61B 5/686* (2013.01)
USPC ......................................................... 607/62

(58) Field of Classification Search
None
See application file for complete search history.

(56) References Cited

U.S. PATENT DOCUMENTS

| | | | |
|---|---|---|---|
| 4,297,685 | A | 10/1981 | Brainard, II |
| 4,365,633 | A | 12/1982 | Loughman |
| 4,543,955 | A | 10/1985 | Schroeppel |
| 4,550,736 | A | 11/1985 | Broughton et al. |
| 4,566,456 | A | 1/1986 | Koning et al. |

(Continued)

FOREIGN PATENT DOCUMENTS

| | | |
|---|---|---|
| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Christopher D Koharski
*Assistant Examiner* — Nadia A Mahmood
(74) *Attorney, Agent, or Firm* — Beth L. McMahon

(57) ABSTRACT

One embodiment relates to a medical device including a sensor to provide signals indicative of a detected posture state of a patient. A memory stores one or more defined vectors, each defined vector being associated with a tolerance describing a relationship with the defined vector. A processor determines a respective similarity between the detected vector and each of one or more of the defined vectors and classifies a posture state of the patient based on whether any similarity has a relationship to the respective defined vector that is described by the associated tolerance. In one embodiment, the similarity is determined without regard to a coordinate system of the patient. Another embodiment relates to determining the similarity based on at least one of an inner product, a length of the defined posture vector and a length of the detected vector.

62 Claims, 20 Drawing Sheets

(56) References Cited

U.S. PATENT DOCUMENTS

| | | |
|---|---|---|
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen et al. |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend et al. |
| 6,853,863 B2 | 2/2005 | Carter et al. |
| 6,878,121 B2 | 4/2005 | Krausman et al. |
| 6,879,352 B1 * | 4/2005 | Kim ............................ 348/807 |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie et al. |
| 7,043,305 B2 | 5/2006 | KenKnight et al. |
| 7,054,687 B1 | 5/2006 | Andersen et al. |
| 7,066,910 B2 | 6/2006 | Bauhahn et al. |
| 7,082,333 B1 | 7/2006 | Bauhahn et al. |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 * | 12/2006 | Koh et al. .................. 607/60 |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |

(56) References Cited

U.S. PATENT DOCUMENTS

| | | |
|---|---|---|
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann et al. |
| 7,389,147 B2 | 6/2008 | Wahlstrand et al. |
| 7,395,113 B2 | 7/2008 | Heruth et al. |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi et al. |
| 7,717,848 B2 | 5/2010 | Heruth et al. |
| 7,769,464 B2 | 8/2010 | Gerber et al. |
| 7,792,583 B2 | 9/2010 | Heruth et al. |
| 7,826,981 B2 | 11/2010 | Goode et al. |
| 8,529,448 B2 | 9/2013 | McNair |
| 8,649,862 B2 | 2/2014 | Ludwig et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0253043 A1* | 11/2006 | Zhang et al. .................. 600/512 |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0284979 A1* | 12/2006 | Clarkson ....................... 348/143 |
| 2006/0287686 A1 | 12/2006 | Cullen et al. |
| 2007/0015976 A1 | 1/2007 | Miesel et al. |
| 2007/0032748 A1* | 2/2007 | McNeil et al. ................ 600/595 |
| 2007/0038265 A1 | 2/2007 | Tcheng et al. |
| 2007/0050715 A1 | 3/2007 | Behar |
| 2007/0073355 A1 | 3/2007 | DiLorenzo |
| 2007/0115277 A1* | 5/2007 | Wang et al. .................. 345/419 |
| 2007/0118056 A1* | 5/2007 | Wang et al. .................. 600/595 |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |

(56) References Cited

U.S. PATENT DOCUMENTS

| | | |
|---|---|---|
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson et al. |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1* | 8/2008 | Sanghera et al. ............... 607/28 |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0106210 A1 | 4/2010 | Hedberg et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1391846 A1 | 2/2004 |
| EP | 1437159 | 7/2004 |
| EP | 1731088 | 12/2006 |
| EP | 1731097 A2 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005079487 A2 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE

(56) References Cited

OTHER PUBLICATIONS

Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Psychophysiologie, Universitat Freiburg, Germany, Mar. 2000, 28 pp.
Foldvary-Schaefer, "Sleep Complaints and Epilepsy: the Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems," ICECS 2002, $9^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp. 2008.
Smith et al., "How do sleep disturbance and chronic pain inter-relate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.
PCT/US09/48686: International Search Report and Written Opinion dated Apr. 7, 2010, 16 pp.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.

(56) References Cited

OTHER PUBLICATIONS

U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.
Extended European Search Report, EP Patent No. 13177656.9, dated Sep. 4, 2013, 7pps.

* cited by examiner

POSTURE STATE CLASSIFICATION FOR A MEDICAL DEVICE

RELATED APPLICATIONS

The following application claims priority to provisionally-filed U.S. Patent Application entitled "Posture State Detection System and Method", Patent Application Ser. No. 61/080,049 filed Jul. 11, 2008, which is incorporated herein by reference in its entirety.

The current application includes subject matter related to the following patent applications, which are incorporated herein by reference in their entireties:

"Posture State Classification for a Medical Device", U.S. Patent Publication Number 2010/0010583 published Jan. 14, 2010 filed on even date herewith;

"Reorientation of Patient Posture States for Posture-Responsive Therapy", U.S. Patent Publication Number 2010/0010383 published Jan. 14, 2010; and "Posture State Detection Using Selectable System Control Parameters", U.S. Patent Publication Number 2010/0010384 published Jan. 14, 2010.

TECHNICAL FIELD

The invention relates to posture detection techniques, and more particularly, to medical devices that detect posture states.

BACKGROUND

A variety of types of medical devices are used for chronic, e.g., long-term, provision of therapy to patients. As examples, pulse generators are used for provision of cardiac pacing and neurostimulation therapies, and pumps are used for delivery of therapeutic agents, such as drugs. Typically, such devices provide therapy continuously or periodically according to parameters. For instance, a program comprising respective values for each of a plurality of parameters may be specified by a clinician and used to deliver the therapy.

It may be desirable in some circumstances to activate and/or modify the therapy based on a patient state. For example, the symptoms such as the intensity of pain of patients who receive spinal cord stimulation (SCS) therapy may vary over time based on the activity level or posture of the patient, the specific activity undertaken by the patient, or the like. It is desirable to be able to detect and classify the state of the patient accurately so that this classification may be used to activate and/or select a therapy that is most efficacious for that state.

SUMMARY

According to one aspect of the disclosure, techniques are provided for classification of a posture of a patient. Posture classification occurs using a coordinate system of the sensor, which may be an accelerometer or some other sensor for detecting posture (e.g., gyroscope, pressure transducer, etc.). This posture classification occurs, in one embodiment, without regard to the coordinate system of the patient's body. As a result, no conversion or transformation need occur to transfer the sensor output signals into a coordinate system of the body. Instead, the sensor output signals may be used as a vector, and directly compared against defined posture definitions. This significantly decreases the time required to classify a patient's posture.

In one embodiment, a sensor, which may include one or more accelerometers, is implanted, or otherwise carried by a patient. The sensor provides a three-dimensional vector indicative of a posture of the patient. As previously stated, this vector is expressed in the coordinate system of the sensor without regard to the coordinate system of the patient's body.

While the sensor is being carried by the patient in a substantially-fixed position, various postures may be defined as follows. A patient assumes a posture and a vector is obtained from the sensor. This vector is associated with the posture that is being defined. This vector may be referred to as a defined posture vector.

Next, a user (e.g., a clinician) may select a tolerance for use with the posture under definition. The tolerance describes a distance relationship to the vector. In one embodiment, this tolerance may be expressed as an angle defining a cone surrounding the posture vector. This distance may alternatively be an absolute distance, a Euclidean distance, a city-block distance, a trigonometric description (e.g., sine or cosine), and so on that specifies a distance from the defined posture vector. This tolerance is associated with the posture definition.

Any number of posture definitions may be created in the foregoing manner. These posture definitions may then be used to classify a patient's posture as follows. While the sensor is disposed in relation to the patient's body in substantially the same manner as it was carried during the posture definition process, a vector is obtained from the sensor indicative of the patient's current posture. This vector, referred to as a detected posture vector, is expressed in terms of the coordinate system of the sensor without regard to the coordinate system of the patient's body. As such, this vector may be compared directly to the vectors contained within the posture definitions, and no transformation of the detected posture vector need be performed before the patient's posture may be classified. This greatly improves the efficiency of posture classification, since transposing the sensor signals to be in a coordinate system of a patient's body is a processing-intensive operation.

According to another aspect, posture classification may be optimized even further by eliminating angle derivations during the posture classification process. While some techniques derive angles to determine a patient's posture, a method which is processing intensive and/or may require a large expenditure of other resources (e.g., as when look-up tables are used for angular approximations), the current disclosure instead derives non-angular "similarity" metrics to perform posture classification. In particular, classification of a posture is performed by determining a non-angular similarity between a detected posture vector and a defined posture vector of a defined posture. Such a similarity may be expressed as a trigonometric function (e.g., sine or cosine), a Euclidean distance, an absolute distance, a city-block distance, or some other type of non-angular measure. If this derived similarity meets the requirements specified by the tolerance for the defined posture, the patient may be classified as being in this posture.

In one embodiment, a similarity between a detected posture vector and a defined posture vector may be based on a squared length of the defined posture vector and the inner product between the defined posture vector and the detected posture vector. The former value, the squared length of the defined posture vector, is a constant that is only required to be calculated once after the defined posture vector is selected during posture definition. Thereafter, posture classification may be completed using the pre-derived constant and an inner product calculation. This type of processing may be completed very quickly using far fewer processing steps than are needed when angle calculations are made to classify postures, as is necessary in prior art classification techniques. This is significant in applications such as those associated with implantable medical devices that have a limited power supply.

According to a more specific embodiment, the comparison step may compare a detected posture vector to one or more defined posture vectors for one or more defined postures. This comparison identifies to which of these defined posture vectors the detected posture vector is closest. The patient may then be classified as being in the posture associated with this closest defined posture vector. According to one aspect, this comparison may only require determination of the inner products between the detected posture vector and the defined posture vectors. In a case wherein only a single one of these derived inner products is positive, it may be determined that the patient is in the posture associated with the defined posture vector yielding the positive inner product. This is a particularly efficient mechanism for performing posture classification, since derivation of inner products can be completed with very few processing steps.

According to another aspect of the disclosure, in some cases a first defined posture may be associated with a defined posture vector and multiple tolerances. Each of these multiple tolerances may describe a respective relationship with the defined posture vector. During posture classification according to this method, the detected posture vector may be compared to one or more of the defined posture vectors for other defined postures. Based on the result of this initial comparison, one of the multiple tolerances is selected for use in determining whether the patient is in the first defined posture.

As a concrete example of the foregoing, consider a patient that may be leaning some distance from a defined posture vector associated with an Upright posture. It may be desirable to allow the patient to lean a significant amount in the forward direction while still allowing the patient to be classified in the Upright posture. In contrast, it may be desirable to allow only a small amount of backward leaning before the patient is re-classified in a posture other than the Upright posture. Because of this non-symmetrical requirement, a single tolerance, or relationship, with the Upright defined posture vector cannot adequately be used to classify the Upright posture. Instead, two different tolerances are defined, with the larger tolerance being associated with leaning forward, and a smaller tolerance being used for leaning backward.

When using the Upright posture definition of the current example to classify a patient's position, it must first be determined whether the patient is leaning forward or backward relative to the Upright posture. To do this, the detected posture vector is compared to two additional defined posture vectors: a posture vector for the Face Down posture (associated with lying face down) and a posture vector for a Face Up (associated with lying face up). Using this comparison, it is determined whether the detected posture vector is closer to the Face Down posture such that the patient is leaning forward, or is instead closer to the Face Up posture such that the patient is leaning backward. Based on the result, one of the multiple tolerances defined for the Upright posture may be selected. If the detected posture vector is closer to Face Down, a tolerance described a larger distance relationship may be selected to determine whether the patient is still in the Upright posture. Conversely, if the detected posture vector is closer to Face Up, indicating the patient is leaning backwards, a tolerance describing a smaller distance from the Upright posture vector may be used in this classification. In this manner, multiple tolerances, each defining a respective distance relationship, may be associated with a single posture definition.

Other aspects of the disclosure relate to using "virtual" defined posture vectors to define postures. A virtual defined posture vector is a vector that is obtained by applying processing steps to one or more other defined posture vectors. For instance, in one example, a virtual defined posture vector may be derived by obtaining the cross-product of multiple pairs of defined posture vectors and averaging those cross-products. Other types of processing may be used instead to obtain the virtual posture vectors.

Yet another aspect may relate to using logical functions (e.g., an OR-like or an AND-like function) to relate multiple regions in space for use in defining a posture. This allows more complex spatial regions to be used for posture classification.

In some embodiments, a condition may be associated with a posture definition. Evaluation of this condition is performed to select some aspect of the definition. For instance, in one example, the evaluation of the condition produces a result that is used to select a size or shape of a region that surrounds a vector that is referenced by the definition.

Other aspects of the current disclosure relate to classifying an activity state of a patient. Such a classification may relate to activity level (e.g., footfalls), a direction of motion (e.g., direction of velocity or direction of acceleration), or some other measure indicative of motion or activity.

An activity state may be defined using patient participation in a manner similar to that described about in reference to posture definition. A patient carrying a sensor may be directed to begin performing an activity (which may involve motion or lack thereof). One or more raw or processed signals may be obtained from the sensor that are indicative of the activity. In one embodiment, these signals may be obtained from AC components of the sensor signals. These one or more signals may be stored along with the definition of the activity state. In some instances, a user such as clinician may provide additional information to include with the activity state definition. As an example, if the signals provide a vector indicative of velocity or acceleration, the user may supply a tolerance to be used with these signals in much the same way a tolerance is selected for use with a posture vector.

In an alternative embodiment, patient participation need not be employed in the definition of the activity state. In this case, the user (e.g., a clinician) may supply all information that is required for the activity state definition. For instance, a clinician may provide both a vector and a tolerance for use in defining the activity.

After definition of the activity state, the definition may be used to classify movement of a patient. In this case, one or more signals are received from the sensor while the patient is going about a daily routine. These signals may be processed (e.g., filtered to extract AC signal components, etc.) and compared against the defined activity states to determine whether the patient is to be classified as being in this activity state.

As previously noted, one or more of the activity state definitions may include respective vectors, referred to herein as defined activity vectors. To determine whether a patient is in this type of an activity state, a detected activity vector (e.g., velocity or acceleration vector) obtained from the sensor signals may be compared to one or more of the defined activity vectors. This comparison may utilize any of the techniques described herein in regards to posture classification. That is, this comparison may be performed by determining whether the detected activity vector has a distance relationship to a defined activity vector as determined by an associated tolerance. This comparison may be performed without the need to calculate angles, and may further utilize constants stored with the defined activity state. Such constants may include, for instance, a squared length of the defined activity vector in the manner described above. Moreover, if desired, a single activity state definition may include multiple tolerances as discussed above in regards to posture definitions. An activity state definition may likewise employ virtual vectors of logical functions, as was described above with respect to posture definitions.

Posture definitions and activity state definitions may be used together to classify a patient's posture state. That is, a posture state definition may be created for a patient that references at least one of a posture definition and an activity state. For instance, a posture state of Upright and Active may be defined. A patient will be detected as being in this posture state when he is determined to be in an Upright posture and an Active activity state. In this manner, postures and/or activity states are used to classify a patient's position and motion.

Posture state classification may be used to initiate various types of responses. For instance, when a posture state change is detected, a system may automatically modify a therapy that is currently being delivered, or select a new therapy for delivery to the patient. In another embodiment, the detected posture state transition may be used to prompt some notification, or to record some information.

According to one aspect, an implantable medical device is disclosed. The device includes a sensor to provide signals indicative of a detected posture vector of a patient, and a memory to store one or more defined posture vectors. Each defined posture vector is associated with a tolerance describing a relationship with the defined posture vector. The device may further include a processor to determine a respective similarity between the detected posture vector and each of one or more of the defined posture vectors and to classify a posture of the patient based on whether any similarity has a relationship to the respective defined posture vector that is described by the associated tolerance.

A method is also disclosed that involves use of a medical system having a sensor. The method may include obtaining a defined vector indicative of a defined posture state, obtaining from the sensor a detected vector that is indicative of a posture state of a patient, and determining a similarity between the defined vector and the detected vector, the similarity being determined without deriving an angle. The method may also comprise classifying the posture state of the patient based on the similarity and initiating via the medical system an action related to care provided to the patient, the action being based on the classification of the posture state of the patient. This method may be performed via an implantable medical device, such as a device the delivers electrical stimulation therapy to a patient. This method may also be performed by an external medical device, or a processor of an external programmer, such as a patient or clinician programmer.

A medical system may be provided in another embodiment. This system may include a sensor to provide a detected vector indicative of a posture state of a patient, a storage device to store posture state definitions, one or more of which are associated with defined vectors, and a processor. The processor is provided to derive a similarity between the detected vector and each of one or more of the defined vectors, wherein deriving the similarity does not require derivation of angles, and to classify the posture state of the patient based on the derived similarities. A response module may be included to generate a response based on the posture state classification. Such a response may, for instance, provide therapy to a patient, provide notification of various posture classifications (e.g., notify a caregiver that a patient has potentially experienced a fall) or provide some other response.

Another aspect relates to a storage medium for storing instructions to cause a digital processor to obtain a defined vector indicative of a defined posture state, obtain from the sensor a detected vector that is indicative of a posture state of a patient, and determine a similarity between the defined vector and the detected vector. The similarity may be determined without deriving an angle. The instructions further cause the processor to classify the posture state of the patient based on the similarity, and initiate an action related to at least one of caring for, collecting data describing, and diagnosing, the patient.

The details of one or more embodiments of the disclosed techniques are set forth in the accompanying drawings and the description below. Other features, objects, and advantages of the disclosed mechanisms will be apparent from the description and drawings, and from the claims.

DETAILED DESCRIPTION

Techniques described herein relate to classification of a patient's posture state. Such a posture state may involve at least one of a posture and an activity. Classification of a patient's posture state may then be used to initiate a response. For instance, such classification may be used to deliver therapy in a closed-loop manner.

Examples of therapies that may be delivered in a closed-loop manner using techniques presented in the current disclosure include electrical stimulation or the delivery of therapeutic agents. Electrical stimulation may be, for example, used to treat patients that suffer from chronic back pain, leg pain, or other pain that cannot be treated through other methods. As a patient changes posture state, which may involve changes in position and/or activity, the stimulation may need to be adjusted in order to maintain efficacy. Such changes in a patient's posture state may be detected, classified, and used to modify a therapy that is currently being delivered, or to select a new therapy for delivery to the patient. In another embodiment, the detected posture state transition may be used to prompt some notification, or to record some information.

According to some embodiments of the disclosure, a medical device, e.g., an implantable medical device (IMD), includes or is coupled to a sensor that senses a posture state. The sensor may be a three-axis accelerometer such as a piezoelectric and/or micro-electro-mechanical (MEMs) accelerometer. The sensed posture state may then be used to initiate some action, which may be an action to be taken in regards to the patient. This action may merely involve storing the sensed posture state. The action may additionally or alternatively involve a change in delivered therapy, providing a notification, and/or any other action that is usefully taken in regards to the sensed posture state.

The IMD may store a table or other data structure that contains records. Each such record may contain therapy information associated with a respective posture state. The IMD may automatically sense the current posture state of the patient and/or changes in the posture state of the patient. This sensed information may be employed to reference the table or other data structure that contains the therapy information. An appropriate therapy may thereby be selected that provides the most efficacious results for the patient's current posture state.

Figure 1:
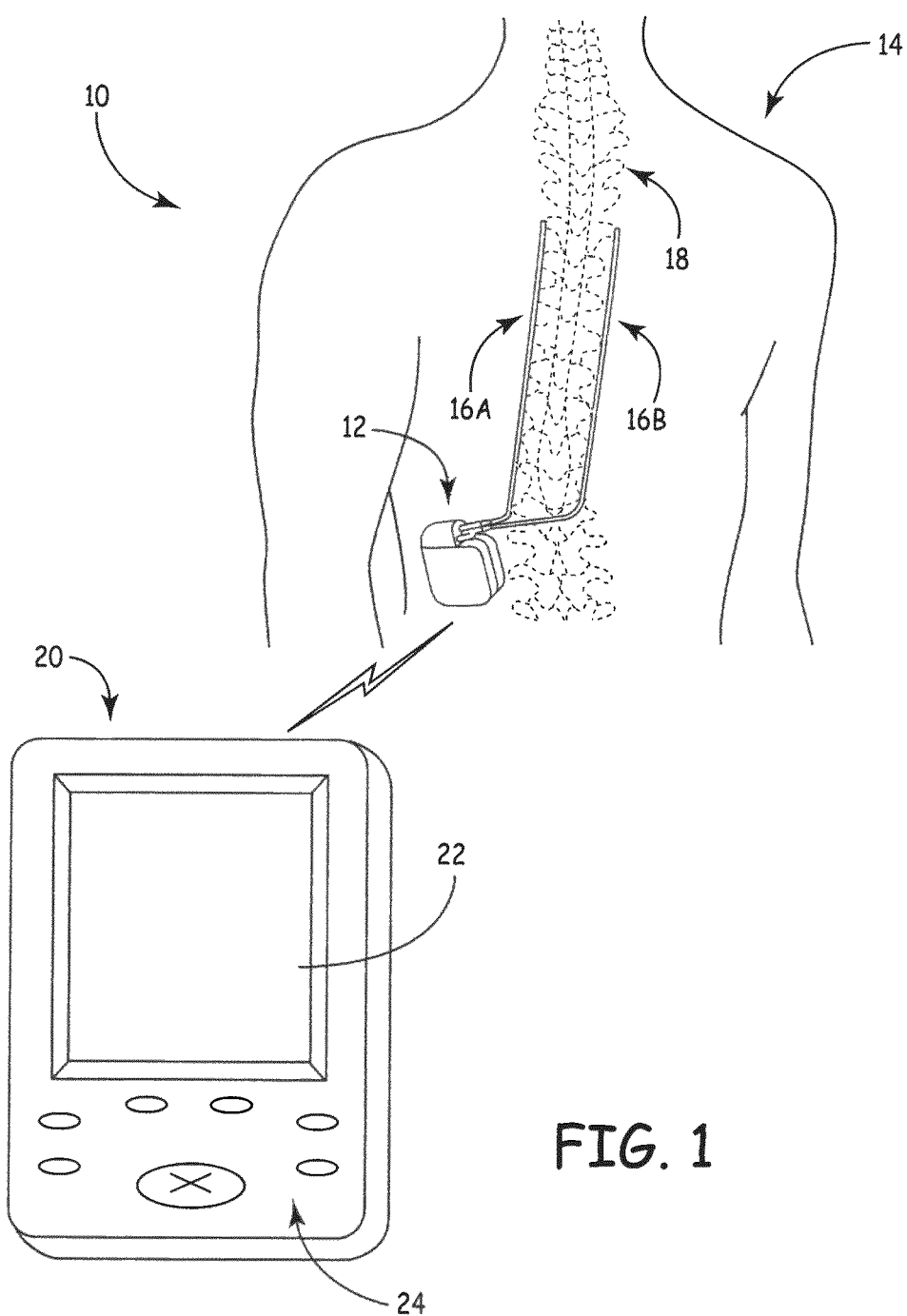
FIG. 1 is a conceptual diagram illustrating an example system that facilitates the definition and classification of posture states according to the disclosure.

FIG. 1 is a conceptual diagram illustrating an example system 10 that facilitates the definition and classification of posture states according to the disclosure. In the illustrated example, system 10 includes an IMD 12, which is implanted within a patient 14, and delivers neurostimulation therapy to patient 14.

IMD 12 delivers neurostimulation therapy to patient 14 via therapy connections 16A and 16B ("therapy connections 16"), which may be leads carrying electrodes, for instance. In this type of application, the electrodes (not shown) may be, e.g., electrode pads on a paddle lead, circular (e.g., ring) electrodes surrounding the body of leads, conformable electrodes, cuff electrodes, segmented electrodes, or any other type of electrodes capable of forming unipolar, bipolar or multipolar electrode configurations for therapy. In some applications, such as SCS to treat chronic pain, the adjacent therapy connections 16 may have longitudinal axes that are substantially parallel to one another, and one therapy connection need not have the same number of electrodes as another therapy connection.

More than two, or only one, of the therapy connections 16 may be provided by the system. In one case, three therapy connections 16 may be provided, each carrying electrodes to form a so-called 4-8-4 or 4-16-4 lead configuration, whereby the numbers indicate the number of electrodes in a particular column, which can be defined by a single lead. Other lead configurations, such as 8-16-8, 8-4-8, 16-8-16, 16-4-16, are also possible. External programmer 20 may be initially told the number and configuration of leads 16 in order to appropriately program stimulation therapy.

Therapy connections 16 may, as shown in FIG. 1, be implanted proximate to the spinal cord 18 of patient 14, and IMD 12 may deliver SCS therapy to patient 14 in order to, for example, reduce pain experienced by patient 14. However, the disclosure is not limited to the configuration of therapy connections 16 shown in FIG. 1 or the delivery of SCS therapy. For example, one or more therapy connections 16 may extend from IMD 12 to the brain (not shown) of patient 14, and IMD 12 may deliver deep brain stimulation (DBS) therapy to patient 14 to, for example, treat tremor, Parkinson's disease, or epilepsy.

As further examples, one or more therapy connections 16 may be implanted proximate to the pelvic nerves, stomach, or other organs (not shown) and IMD 12 may deliver neurostimulation therapy to treat incontinence, gastroparesis, sexual dysfunction or other disorders. Additionally, this disclosure is not limited to implantable devices. Any external medical device may classify posture states for use in delivering therapy according to the techniques of the disclosure.

Further, as discussed above, the disclosure is not limited to embodiments in which IMD 12 delivers stimulation therapy. For example, in some embodiments, IMD 12 may additionally or alternatively be coupled to one or more catheters or other substance delivery devices to deliver one or more therapeutic substances to patient 14, e.g., one or more drugs.

Example therapeutic agents that IMD 12 may be configured to deliver include, but are not limited to, insulin, morphine, hydromorphone, bupivacaine, clonidine, other analgesics, genetic agents, antibiotics, nutritional fluids, hormones or hormonal drugs, gene therapy drugs, anticoagulants, cardiovascular medications or chemotherapeutics. In this case, IMD 12 functions as a drug pump and communicates with external programmer 20 to initialize therapy or modify therapy during operation. In addition, IMD 12 may be refillable to allow chronic drug delivery.

When IMD 12 delivers a therapeutic substance to the patient, multiple therapy connections 16 such as catheters may be located to deliver the substance to the same anatomical location or the same tissue or organ. Alternatively, each catheter may deliver therapy to different tissues within patient 12 for the purpose of treating multiple symptoms or conditions. In some embodiments, IMD 12 may be an external device which includes a percutaneous catheter that provides one of therapy connections 16 or that is coupled to therapy connections 16, e.g., via a fluid coupler. In other embodiments, IMD 12 may be coupled to therapy connections 16 that provide both electrical stimulation and drug delivery therapy.

Although the target therapy delivery site may be proximate to spinal cord 18 of patient 12, other applications are possible. For instance, the target delivery site in other applications of drug delivery system may be located within patient 14 proximate to, e.g., sacral nerves (e.g., the S2, S3, or S4 sacral nerves) or any other suitable nerve, organ, muscle or muscle group in patient 14, which may be selected based on, for example, a patient condition. In one such application, drug delivery system may be used to deliver a therapeutic agent to tissue proximate to a pudendal nerve, a perineal nerve or other areas of the nervous system, in which cases, therapy connections 16 would be implanted and substantially fixed proximate to the respective nerve. Thus, many types of applications are possible.

Also, in some aspects, techniques for evaluating postures and posture states as described herein may be applied to IMDs that are generally dedicated to sensing or monitoring and do not include stimulation or other therapy components. For instance, the posture state classification mechanisms described herein may be used for diagnostic purposes, such as diagnosing a need for therapy, or determining how a patient is responding to existing therapy. Posture state classification may also be used to provide notifications, such as providing notification via a wireless link to a care giver that a patient has potentially experienced a fall. Thus, posture definition and classification according to the current disclosure may be used to initiate many types of actions, including storing the classification for later analysis, initiating a change in therapy, prompting a notification, and so on.

In exemplary embodiments, IMD 12 functions under the control of one or more programs. A program includes one or more parameters that define an aspect of posture classification and/or detection according to that program.

In exemplary embodiments, IMD 12 may initiate actions in response to information within a record. For instance, a plurality of records may be stored in a table or other data structure. Each such record may describe at least one posture state and an associated action that is to be taken in response to detection of this posture state. As discussed above, a posture state is determined based on at least one of a defined posture and an activity component (e.g., a parameter indicative of footfalls). When IMD 12 detects a posture state, IMD 12 may initiate the action that is indicated by the information in the record for that posture state. This action may involve delivery of therapy according to a particular program, group of programs and/or a set of parameters. This action may alternatively or additionally involve providing some notification and/or recording some information.

In the illustrated example, system 10 also includes a programming device 20, which may, as shown in FIG. 1, be a handheld computing device. Programming device 20 allows a user such as a patient or a clinician to interact with IMD 12. Programming device 20 may, for example, communicate wirelessly with IMD 12 using radio-frequency (RF) telemetry techniques, or any other techniques known in the art.

Programming device 20 may, as shown in FIG. 1, include a display 22 and a keypad 24 to allow the user to interact with programming device 20. In some embodiments, display 22 may be a touch screen display, and the user may interact with programming device 20 via display 22. The user may also interact with programming device 20 using peripheral pointing devices, such as a stylus or mouse. Keypad 24 may take the form of an alphanumeric keypad or a reduced set of keys associated with particular functions. In some embodiments, keypad 24 may include an increase amplitude button and a decrease amplitude button to directly adjust stimulation amplitude.

In exemplary embodiments, programming device 20 is a clinician programmer used by a clinician to define postures and posture states according to the current disclosure. The defined postures may then be used to detect postures and posture states that are assumed by the patient during daily life. The detected postures may be used to determine a type of therapy to provide to the patient, to monitor general well-being of the patient, to prescribe new therapies for the patient, and to determine whether the patient has undergone a posture-specific event such as suffering a fall.

Figure 2:
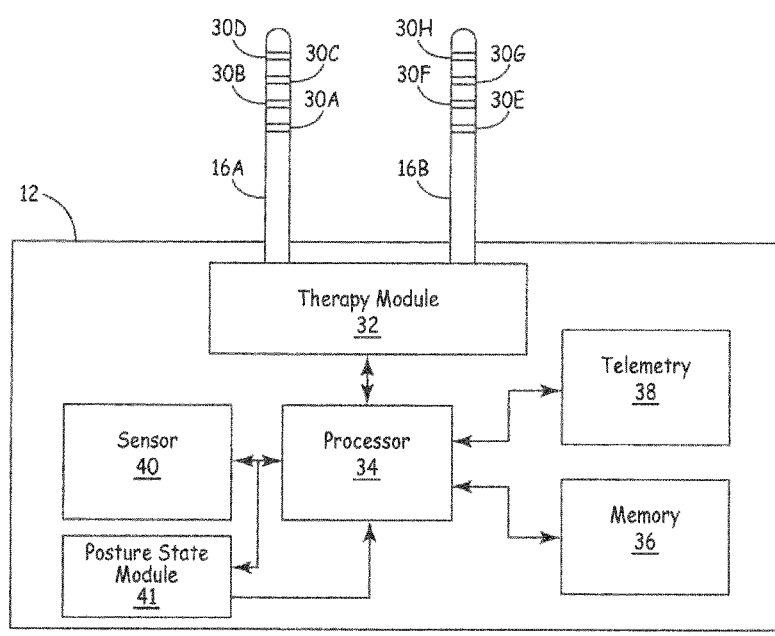
FIG. 2 is a block diagram illustrating one embodiment of an implantable medical device in greater detail.

FIG. 2 is a block diagram illustrating one embodiment of IMD 12 in greater detail. IMD 12 may deliver neurostimulation therapy via therapy connections 16A and 16B. As discussed above, these therapy connections may be leads having one or more electrodes 30A-H (collectively "electrodes 30") or some other therapy mechanism, such as one or more catheters for delivering a substance to a patient. IMD 12 may be coupled to any number of therapy connections.

Therapy connections 16A and 16B are coupled to IMD 12 via therapy module 32. This may be a stimulation pulse generator, for example. Such a pulse generator may be coupled to a power source such as a battery. Therapy module 32 may deliver electrical pulses to patient 14 and/or may deliver some type of substance, such as a drug.

Therapy delivery may occur under the control of a processor 34. Processor 34 may comprise a microprocessor, a controller, a digital signal processor (DSP), an application specific integrated circuit (ASIC), a field-programmable gate array (FPGA), discrete logic circuitry, or any combination thereof.

Processor 34 may control therapy module 32 to deliver neurostimulation or other therapy according to a selected program. For instance, processor 34 may control therapy module 32 to deliver electrical pulses with the amplitudes and widths, and at the rates specified by the program. Processor 34 may also control therapy module 32 to deliver such pulses via a selected subset of electrodes 30 with selected polarities, e.g., a selected electrode configuration, as specified by the program.

Therapy module 32 is a type of module that may be referred to generally as a response module. In addition to, or instead of, therapy module 32, IMD 12 may include other response modules for initiating other types of responses. For instance, a notification module (not shown) may be provided to initiate the issuance of a notification to programmer 20, or to initiate some other type of communication, based on the defined posture or posture state. Alternatively, a module may be provided to initiate storing of patient-specific or system-related data based on the posture or posture state. Thus, IMD 12 may include other types of modules to initiate other types of response in addition to, or instead of, therapy-based responses.

IMD 12 also includes a telemetry circuit 38 that allows processor 34 to communicate with programming device 20. For example, a clinician may select programs, parameters, posture definitions, posture state definitions, and associated therapies and actions that are to be transferred to memory 36 of IMD 12. Processor 34 also communicates with programming device 20 to provide diagnostic information stored in memory 36 to a clinician via telemetry circuit 38. Processor 34 may also communicate with a patient programming device to receive from a user such as patient 14 therapy parameter adjustments or other therapy adjustments, as well as commands to initiate or terminate stimulation. Telemetry circuit 38 may correspond to any telemetry circuit known in the implantable medical device arts.

IMD 12 further includes a sensor 40 to sense one or more parameters used to detect a posture state. In exemplary embodiments, sensor 40 includes a three-axis accelerometer, such as a piezoelectric and/or MEMs accelerometer. In other embodiments, multiple single or multi-axis accelerometers may be employed in place of one three-axis accelerometer. In yet other examples, sensor 40 may include gyroscopes, pressure sensors, or other sensors capable of sensing posture and/or activity levels. Thus, it will be understood that sensor 40 may comprise more than one sensor.

In exemplary embodiments, sensor 40 is located within a housing (not shown) of IMD 12. However, the disclosure is not so limited. In some embodiments, sensor 40 is coupled to IMD 12 via additional therapy connections 16 (not shown). The sensor may be located anywhere within patient 14.

In alternative examples, first and second sensors may be located in different positions within patient 14 and relative to components of IMD 12. For example, one sensor may be an independent implantable sensor that is implanted adjacent to but physically disconnected from IMD 12. Another sensor may be, e.g., connected to an additional sensor lead positioned within patient 14 adjacent therapy connections 16. Alternatively, the other sensor may be an independent implantable sensor that is implanted adjacent to but physically disconnected from therapy connections. In some examples, one posture sensor is arranged proximate a therapy delivery site within patient 14, while another sensor is arranged closer to IMD 12 than the first sensor.

In some embodiments, IMD 12 may be coupled to one or more accelerometers or other position sensors located at various positions on the external surface of patient 14. In yet other embodiments, these one or more sensors may communicate wirelessly with IMD 12 instead of requiring one or more leads to communicate with the IMD. For example, sensor 40 may be located external to patient 14 and may communicate wirelessly with processor 34, either directly or via programming device 20.

As previously mentioned, sensor 40 senses one or more parameters that are used to detect a posture state. A posture state is a state that is classified by at least one of a posture definition and an activity state, where the activity state may describe, for example, an overall activity level, an activity level in one or more selected directions, a vector associated with velocity or acceleration, and so on.

Example posture states that may be detected include an Upright posture state. This posture state may be defined as that occurring when the patient is in an upright posture without regard to an activity state. As another example, an Upright and Active posture state may be associated with an upright posture and an activity state that is associated with an activity level above some predetermined threshold level, for instance. Additional exemplary posture states such as "Running", "Sitting", "Bending Over", and so on, may be defined and subsequently sensed by sensor 40.

IMD 12 also includes a memory 36, which may store programmed instructions that, when executed by processor 34, cause IMD 12 to perform the functions ascribed to IMD 12 herein. Memory 36 may include any volatile, non-volatile, magnetic, optical, or electrical media, such as random access memory (RAM), read-only memory (ROM), non-volatile RAM (NVRAM), electrically-erasable programmable ROM (EEPROM), flash memory, and the like.

FIG. 2 further includes posture state module 41 that is provided in one embodiment to process the analog output of sensor 40. Posture state module 41 may include discrete components, a microprocessor, a controller, a digital signal processor (DSP), an application specific integrated circuit (ASIC), a field-programmable gate array (FPGA), and/or the like. Posture state module 41 may operate alone, or in conjunction with processor 34, to process the sensor output for use in detecting a posture state. As an example, posture state module 41 may process the raw signals provided by sensor 40 to determine activity counts indicative of activity level, velocity along one or more accelerometer axis (as may be obtained by integrating the respective accelerometer signal), and so on, for use in detecting a posture state. This is discussed further below.

In other embodiments, posture state module 41 may additionally or alternatively be configured to sense one or more physiological parameters of patient 14. For example, physiological parameters may include heart rate, electromyography (EMG), an electroencephalogram (EEG), an electrocardiogram (ECG), temperature, respiration rate, or pH. These physiological parameters may be used by processor 34, in some embodiments, to confirm or reject changes in sensed posture state that may result from vibration, patient travel (e.g., in an aircraft, car or train), or some other false positive posture state detection by posture state module 41.

Figure 3:
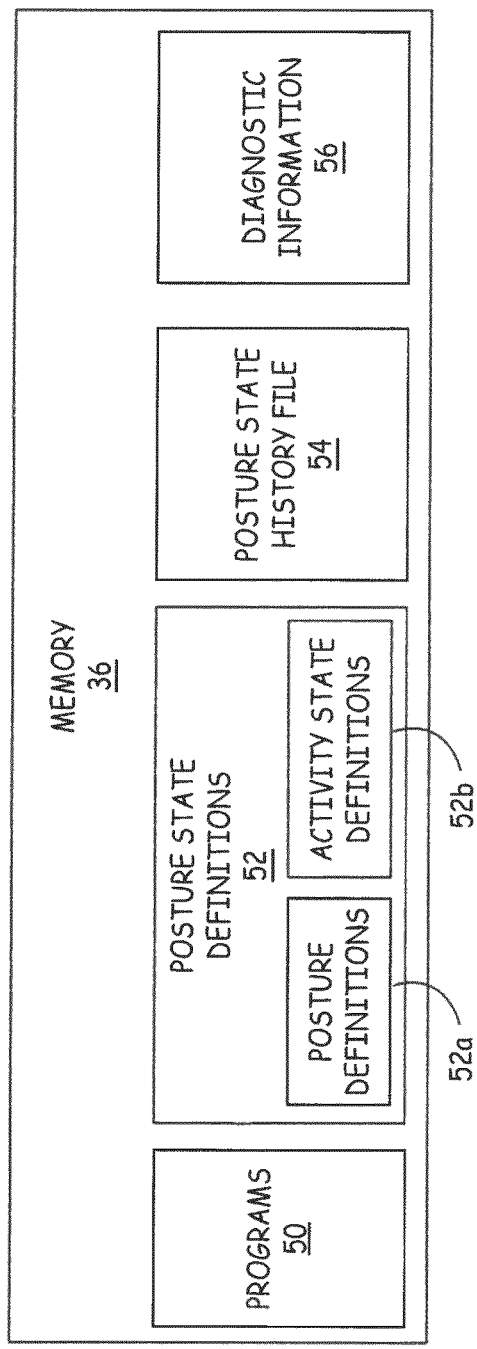
FIG. 3 is a block diagram illustrating an exemplary configuration of a memory of an implantable medical device according to an embodiment of the disclosure.

FIG. 3 is a block diagram illustrating an exemplary configuration of memory 36 of IMD 12. As illustrated in FIG. 3, memory 36 stores programs 50, one or more of which processor 34 may employ to create posture state definitions 52. As discussed above, each posture state definition 52 is associated with at least one of a posture definition 52a and an activity state definition 52b.

A patient's posture, activity state, and/or posture state may be recorded in a posture state history file 54. This file may record, for instance, the patient's current posture information, including current posture and activity states as well as previous posture and activity states assumed by the patient over some period of time.

Memory 36 may also store diagnostic information 56 for use in determining how a patient is responding to therapy, whether therapy modification is needed, whether therapy is to be initiated, and so on.

In some cases, posture state information may be communicated to an external device such as an external monitor which is used to track a patient's condition. Alerts may also be transmitted in this manner. For example, a warning may be transmitted indicating the patient has potentially taken a fall.

As discussed above, the signals of sensor 40 are used to detect a posture. For purposes of this discussion, it will be assumed sensor 40 is a three-axis accelerometer, although sensor 40 could comprise multiple single-axis accelerometers instead, or be another type of sensor such as a gyroscope. Sensor 40 provides a respective signal describing acceleration along each of the x, y, and z axis. These axes will be assumed to be orthogonal.

Each of the x-, y-, and z-axis signals provided by sensor 40 has both a DC component and an AC component. The DC components describe the gravitational force exerted upon the sensor, and can thereby be used to determine orientation of the sensor within the gravitational field of the earth. According to the current disclosure, the orientation of the sensor remains relatively fixed with respect to the patient such that the DC components of the x, y and z signals may be utilized to determine the patient's orientation within the gravitational field, and to thereby determine the posture of the patient.

Prior art mechanisms generally utilize a patient's body coordinate system when determining posture. A body coordinate system may include the superior-inferior (S-I) body axis (extending toe to head), the anterior-posterior (A-P) body axis (extending back to front), and the lateral-medial (L-M) body axis (extending right to left). Postures may be readily defined in terms of these body coordinate axes.

In a simple scenario, a sensor 40 may be positioned within, or on, a patient such that the x, y, and z axes of sensor 40 are aligned with the patient's body coordinate system. In one example, the y axis of sensor 40 may be aligned with the S-I body axis, the z axis of sensor 40 may be aligned with the A-P body axis, and the x axis of sensor 40 may be aligned with L-M body axis. When such an alignment between the sensor coordinate system and body coordinate system can be achieved, the sensor signals may be readily used to detect a posture that is defined in terms of the body coordinate system. However, such alignment may be difficult to achieve and maintain. For instance, sensor position may shift while it is being carried within, or on, the patient.

Another approach to posture classification involves using a correction factor that takes into account that sensor 40 may not be aligned with the body coordinate system. This correction factor, which is used to translate sensor output into the body coordinate system, may be expressed in several ways. For instance, the correction factor may be a transfer matrix that is applied to the sensor output. Alternatively, the correction factor may include pitch, roll and yaw angles that are applied to the sensor signals to perform this transformation. Other mechanisms are possible for expressing the correction factor. According to this approach, the sensor signals may only be used to detect posture after the correction factor is applied and the signals have been expressed in terms of the patient's body coordinate system.

Figure 4:
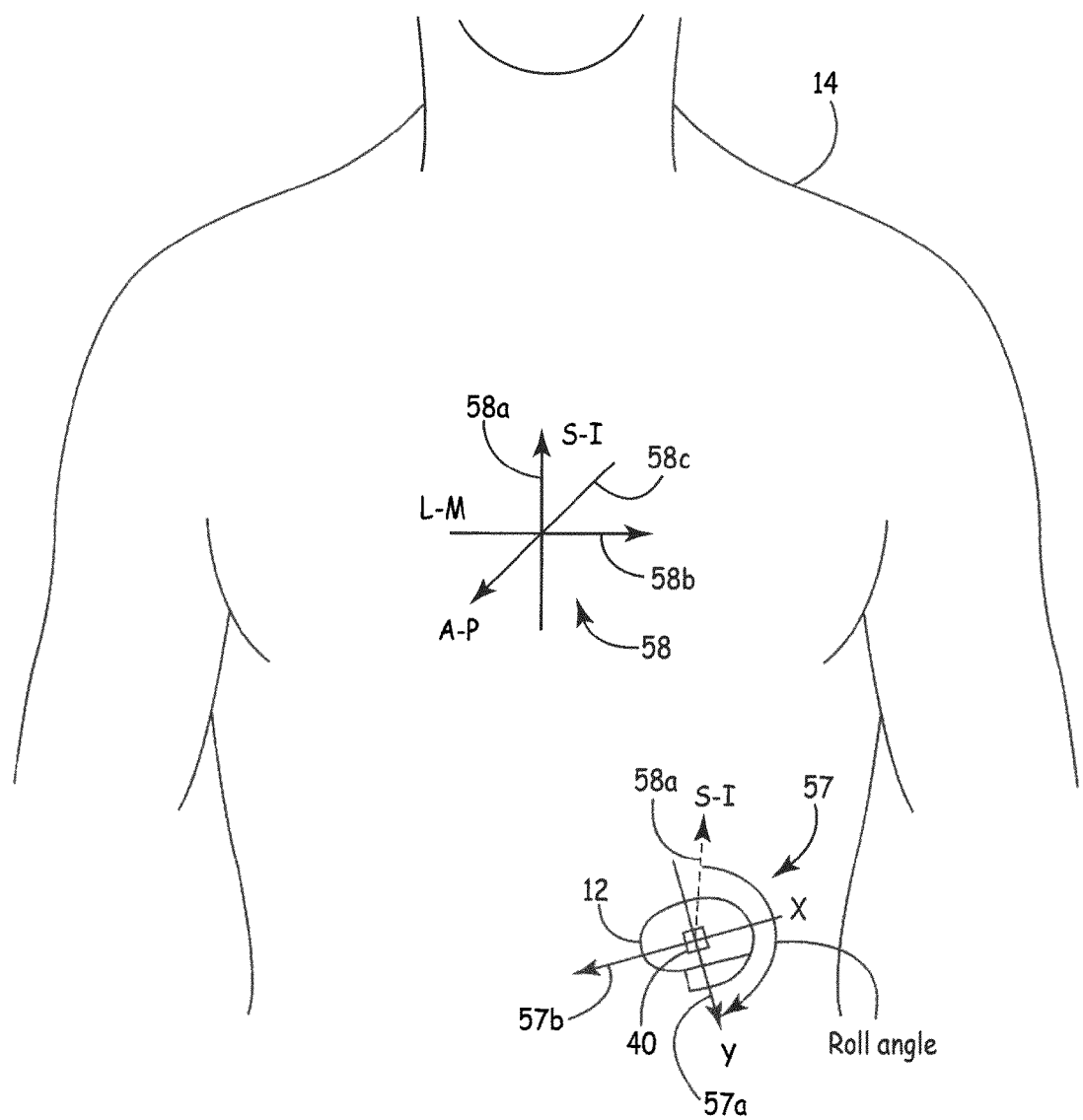
FIG. 4 illustrates the use of a correction factor to translate sensor signals from a sensor coordinate system into a body coordinate system.

FIG. 4 illustrates the use of a correction factor to translate sensor signals from a sensor coordinate system into a body coordinate system. IMD 12 is shown implanted within patient 14. As discussed above, sensor 40 is carried inside housing of IMD 12. Sensor 40 has a sensor coordinate system 57 that includes y axis 57a, x axis 57b, and z axis (not shown for simplicity.)

Patient 14 has a body coordinate system 58 that includes S-I axis 58a, L-M axis 58b, and A-P axis 58c. This body coordinate system 58 is not aligned with the sensor coordinate system in FIG. 4. For instance, the S-I axis 58a does not align with y axis 57a of the sensor coordinate system, and the L-M axis 58b does not align with the x axis 57b of the sensor coordinate system. Therefore, the output of sensor 40 cannot be used to directly detect postures that are defined in terms of the body coordinate system.

Before the output of sensor 40 can be used to detect postures defined in terms of the body coordinate system, a correction factor must be applied to the sensor output. In this example the correction factor includes the roll angle 59. The roll angle describes the misalignment of the S-I axis 58a and the y axis 57a of sensor 40. Similar angles may be used to describe any misalignment between the L-M axis 58b and the x axis 57b, and any misalignment between the A-P axis 58c and the z axis (not shown) of the sensor 40. Mechanisms for applying correction factors are provided, for example, in commonly-assigned U.S. Pat. No. 6,044,297 entitled "Posture and Device Orientation and Calibration for Implantable Medical Devices".

This application of the correction factor to a sensor output may be processing intensive. Moreover, the correction factors must be initially determined. In an IMD that will perform posture classification on a regular basis, it may be desirable to eliminate these steps to conserve power.

According to some embodiments of the disclosed posture detection mechanism, the current techniques may define postures in the coordinate system of the sensor rather than in the patient's body coordinate system. Therefore, there is no correction factor that need be applied to the output of sensor 40. Moreover, the correction factors do not need to be derived. This dramatically simplifies the process of performing posture detection, and thereby saves a significant amount of power and processing time. This is particularly important for devices such as IMDs that have a limited power supply (e.g., rechargeable or non-rechargeable batteries).

To define postures in the coordinate system of the sensor, sensor 40 is positioned on, or in, patient 14 in any orientation in a substantially fixed manner. For instance, the sensor may have been implanted in the patient during a surgical procedure, may have been located on the patient using a transcutaneous procedure, may be temporarily or permanently affixed to an external surface of the patient, or may be carried on the patient's clothing or other articles donned by the patient. The orientation of the sensor relative to the patient is substantially unchanging, at least over some period of time during which posture classification will occur.

Once the sensor is disposed in relation to the patient's body, the patient is asked to temporarily assume a posture. Outputs from sensor 40 are obtained while the patient is in the assumed posture. In the case of a three-axis accelerometer, these outputs define a vector in three-dimensional space that may, in one embodiment, be expressed in terms of the coordinate system of sensor 40 without regard to the coordinate system of the patient's body. This vector that is defined by the output of sensor 40 may be any vector in three-dimensional space.

Next, the vector, which may be referred to as a defined posture vector, is associated with the posture that the patient has been asked to assume. This association may occur by storing the defined posture vector or some representation thereof with a designation that identifies the posture. Such an association may be stored within a table or some other aggregation of data shown as posture definitions 52a of FIG. 3.

The patient may be asked to assume any number of postures in the foregoing manner. As each posture is assumed, signals are obtained from sensor 40 that are indicative of a defined posture vector that are, in one embodiment, expressed in the coordinate system of sensor 40 without regard to the coordinate system of the patient. The defined posture vector or a representation thereof is associated with the posture under definition.

After a defined posture vector is associated with a posture, a tolerance may be selected. This tolerance defines a relationship to the defined posture vector. This relationship may describe a cone, a toroid, or some other region that surrounds or is otherwise disposed in relation to the posture vector, as will be disclosed below in reference to the remaining figures. Like the defined posture vector, this selected tolerance is associated with the posture. Together, the defined posture vector and the tolerance will be used to determine whether a patient has assumed the associated posture.

A patient may use a programming device such as clinician programming device 20 to define a posture. For instance, a user may issue a command via programming device 20 to IMD 12 when a patient has assumed a desired position. This command causes IMD 12 to obtain signal values from sensor 40, which are optionally processed by posture state module 41 of IMD and stored in memory 36. These sensor signals may also be uplinked via telemetry circuitry 38 to an external device such as programming device 20 to undergo some of the processing steps. The captured sensor signals may be associated with an indication (e.g., an alpha-numeric tag, a binary tag, etc.) identifying a posture as specified by a user employing programming device 20. Such an indication may be provided using display 22, keypad 24, a touch screen, a peripheral pointing device, and/or other types of user interface mechanisms, as described above. A user interface such as a graphical user interface may be employed during this process. A tolerance may likewise be specified by the user for association with this posture definition. The associations may be stored in memory of programming device 20, in memory 36 of IMD 12, or in some other storage facility. Techniques for defining a posture vector and creating the above-described associations are described in Patent Application "Posture State Classification for a Medical Device" referenced above and incorporated herein by reference in its entirety.

In the foregoing manner, one or more postures are defined. Each posture is associated with a vector and a tolerance. These defined postures may then be used to classify a patient's positions and movements. As may be appreciated, during this classification process, it is important that sensor 40 be maintained in substantially the same position relative to the patient as existed when the posture definitions were originally obtained. This will allow the same sensor coordinate system that was used to define the postures to likewise be used to classify a patient's positions. If the sensor orientation relative to the patient changes, as may occur if an IMD 12 rotates with respect to patient 14, recalibration of the defined postures must be performed. This will involve again obtaining and re-recording vectors associated with each defined posture in the coordinate system of sensor 40. Techniques for recalibrating posture vectors are described in commonly-assigned Patent Application Ser. No. 61/080,106 referenced above.

After being created in any of the above-described ways, posture definitions may be used to classify a posture of a patient as follows. As a patient moves and/or assumes a posture, outputs from sensor 40 are processed by posture state module 41 to obtain measurements that define a detected posture vector. In one embodiment, this detected posture vector, like the defined posture vector, is expressed in terms of the sensor coordinate system without regard to the patient coordinate system. For this reason, the detected posture vector may be compared directly to one or more of the defined posture vectors without the need to apply a correction factor to the detected posture vector. This comparison indicates whether the detected posture vector has a relationship to any of the defined posture vectors that is specified by an associated tolerance.

As an example, assume a tolerance describes a cone surrounding a defined posture vector and indicates that the detected posture vector must lie within the cone to satisfy the requirements of the definition. The comparison step will determine whether the detected posture vector lies within the cone.

As previously mentioned, if the detected posture vector and the defined posture vectors are expressed in terms of the sensor coordinate system without regard to the patient coordinate system, this classification step does not involve applying any correction factor to the detected posture vector. A direct comparison may be performed between the detected and the defined posture vectors because both vectors are described in terms of the sensor coordinate system. This comparison may be completed in a manner that is not processing intensive and does not require a large expenditure of system resources.

Figure 5A:
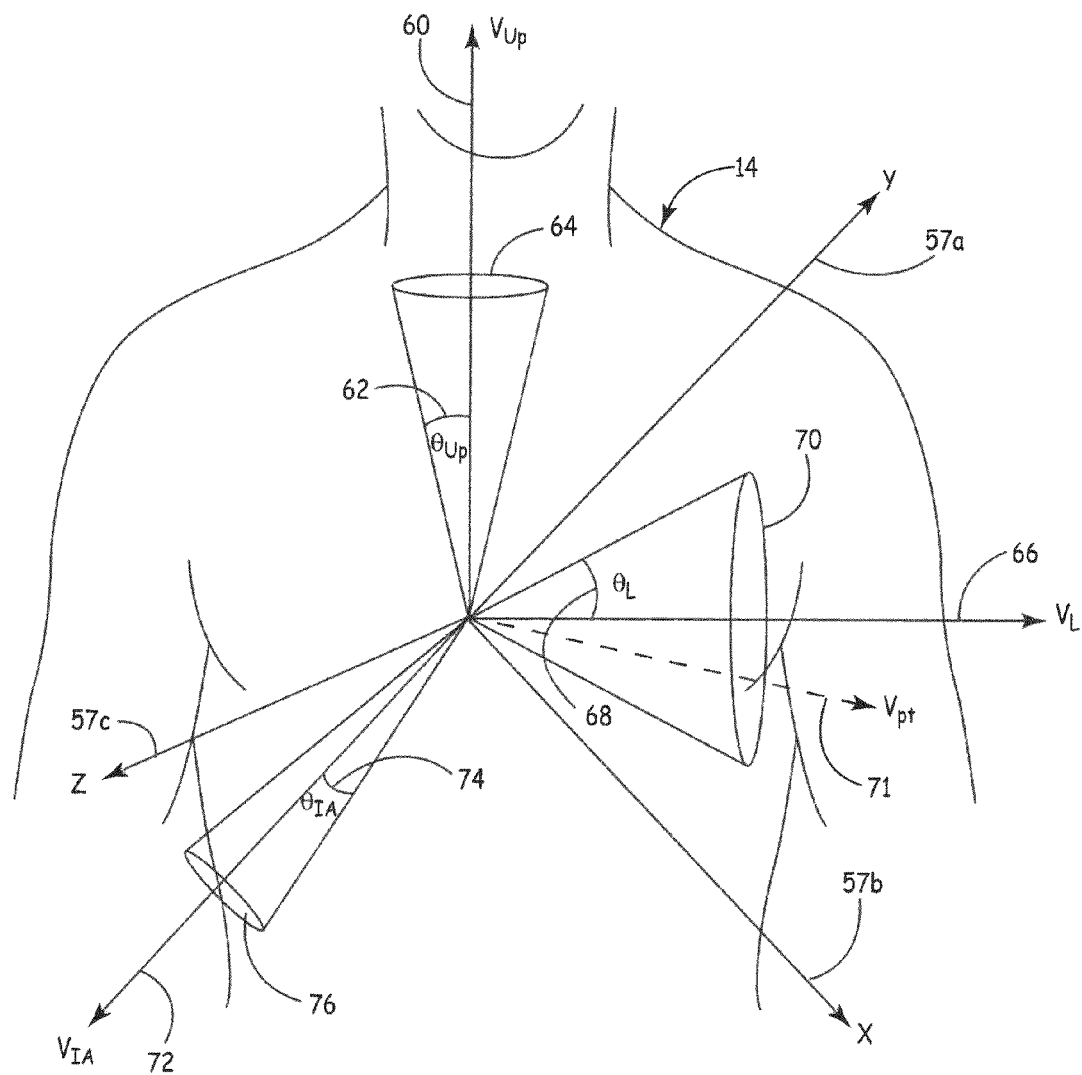
FIG. 5A is a graph illustrating one exemplary method of posture definition.

FIG. 5A is a three dimensional graph illustrating one method of defining postures using sensor 40. Sensor 40 (not shown) is disposed in a substantially fixed manner relative to patient 14. The coordinate system of sensor 40 includes y axis 57a, x axis 57b, and z axis 57c. As described previously, in one embodiment, this sensor coordinate system need not be orientated in any particular manner relative to patient 14 or the patient's body coordinate system 58 (FIG. 4).

When it is known that patient 14 is in an upright position, sensor 40 will provide outputs that can be processed to obtain a vector $[V_1, V_2, V_3]$ which is shown as $V_{Up}$ 60. For purposes of this disclosure, this vector and similar vectors are described using a notation wherein the first vector component (e.g., $V_1$) may correspond to an x-axis component of the vector, the second vector component (e.g., $V_2$) may correspond to a y-axis component of the vector, and the third vector component (e.g., $V_3$) may correspond to a z-axis component of the vector.

Vector $[V_1, V_2, V_3]$ may be associated with an Upright posture, as by storing some indication of this posture along with one or more values identifying the vector. A tolerance may then be selected for this posture that describes a relationship to vector $V_{Up}$. In the current example, the tolerance relates to a cone 64 defined by an angle $\theta_{Up}$ 62. For purposes of this posture definition, the cone identifies a maximum distance from vector $V_{Up}$. So long as a patient's detected posture vector lies within this cone, the patient will be considered to be in the Upright posture. Thus, the patient may be leaning slightly forward, backward, or sideways from the vector $V_{Up}$, but may never-the-less be categorized as standing so long as the detected posture vector lies within cone 64.

Posture vector $V_{Up}$ 60, the predetermined angle $\theta_{Up}$ 62, and some description of the relationship to be identified by the tolerance (e.g., "within the cone") may be associated with the Upright posture for use in later classifying a patient's posture. This may involve storing this information as one of posture definitions 52a (FIG. 3) in memory.

In a similar manner, other posture vectors may be defined. For instance, a vector $V_L$ 66 may be defined that will be used to determine a Left Side posture in which the patient 14 will be classified when he is lying on his left side. In a manner similar to that described above, a tolerance is defined for this vector that may involve a cone 70 having a size indicated by angle 68. As with the Upright posture, this cone indicates a maximum distance from $V_L$ 66. When a detected posture vector lies within this posture cone 70, the patient 14 will be classified as lying on his left side. This is the case for detected posture vector $V_{pt}$ 71, which is shown to be within cone 70.

Any other one or more postures may be defined in a similar manner. As one example, a vector $V_{IA}$ 72 may be associated with a posture that a patient may assume when lying face down with his head somewhat below his feet. A tolerance may be selected for this posture that involves a cone 76 defined by angle $\theta_{IA}$ 74. If a detected posture vector lies within this cone, the patient will be classified as occupying this posture.

Some space may not be included within any posture definition. For instance, in this illustration, space outside of cones 64, 70 and 76 is excluded from a posture definition. This space represents an unclassified posture. In one embodiment, if a detected posture vector falls within this space, the patient is categorized as being in an Undefined posture. In another embodiment, when a detected posture vector falls within this space, the patient's posture may remain classified as it was prior to the time the patient's detected posture vector entered this space. For instance, if the patient was previously classified as being in the Upright posture, the patient may remain classified in the Upright posture after the detected posture vector transitions into the space that is not associated with a defined posture. Thus, in this latter embodiment, the space associated with an Undefined posture may be referred to as "hysteresis space" since it adds hysteresis to the system. The size of this space will vary depending on the number of posture definitions in use within the system, as well as the size of the tolerance associated with each posture definition.

According to other scenarios, the posture definitions may not be mutually exclusive. For instance, although none of the areas of cones 64, 70 and 76 overlap in FIG. 5A, overlap of areas associated with different posture definitions is possible in another embodiment. If such overlap exists, it is possible for a patient to be classified as being in more than one posture at once, as will be described further below.

In the foregoing manner, any vector may be selected for use in defining a posture. Each defined posture vector need not be in any particular plane or have any predetermined relationship to any other defined posture. As another example, an Upright posture need not be orthogonal to a Lying Down posture. Moreover, postures assumed while the patient is reclining (e.g., Right Side, Left Side, Face Up, Face Down, etc.) need not be co-planar. As still another illustration, a Right Side posture defined to describe a patient lying on his right side need have no particular relationship to the Left Side posture that is discussed in regards to FIG. 5A.

Using the techniques described above, posture definitions may be created that are specific to a particular patient's activities and/or profession. For instance, a bank teller may spend a significant portion of his working day leaning forward at a particular angle. Therefore, sensor 40 may be used to obtain a defined posture vector that is specific to this Leaning posture. Similarly, a tolerance may be selected for this posture definition that is specific to the particular patient. Thereafter, classification of the patient's position in this Leaning posture may be used to trigger delivery of therapy, recordation of patient information and/or some other type of action. As previously discussed, in one embodiment, all defined posture vectors may be defined in the coordinate system of sensor 40 and without regard to a patient's body coordinate system to provide for efficient posture classification.

All of the above examples of posture definitions describe a cone. The size of a cone may be described by an angle of the cone. For instance, the size of cone 64 is described by angle $\theta_{Up}$ 62. While the angles may be selected to be of any size, in one embodiment, angles may be generally between approximately 1 degree and approximately 70 degrees. In other examples, cone angles may be between approximately 10 degrees and approximately 30 degrees. In some examples shown in FIG. 5A, the cone angles are approximately 20 degrees.

Another way to specify a cone is by selecting a radius of a base of a cone relative to a center vector or axis. This radius may, but need not, be symmetrical about the associated defined posture vector. In the example shown in FIG. 5A, cones 64, 70, and 76 each has rotational symmetry about the respective center axis 60, 66, and 72. Thus, FIG. 5A illustrates cones in which center lines 60, 66, and 72 pass perpendicularly through the centers of the respective base. In other examples, center lines 60, 66, 72 may not pass perpendicularly through the centers of the respective base. Thus, in the case of tolerances that describe cones, the cones may be any one of multiple possible configurations.

When posture definitions reference cones, the definition may indicate that the patient will be classified as occupying the posture when the patient's detected posture vector is within the cone (i.e., the detected posture vector is no more than the maximum distance described by the cone from the defined posture vector). However, this need not be the case, and the patient may instead be classified as occupying an associated posture if a sensor reading is outside of (rather than inside of) a cone, as described in reference to FIG. 5B.

Figure 5B:
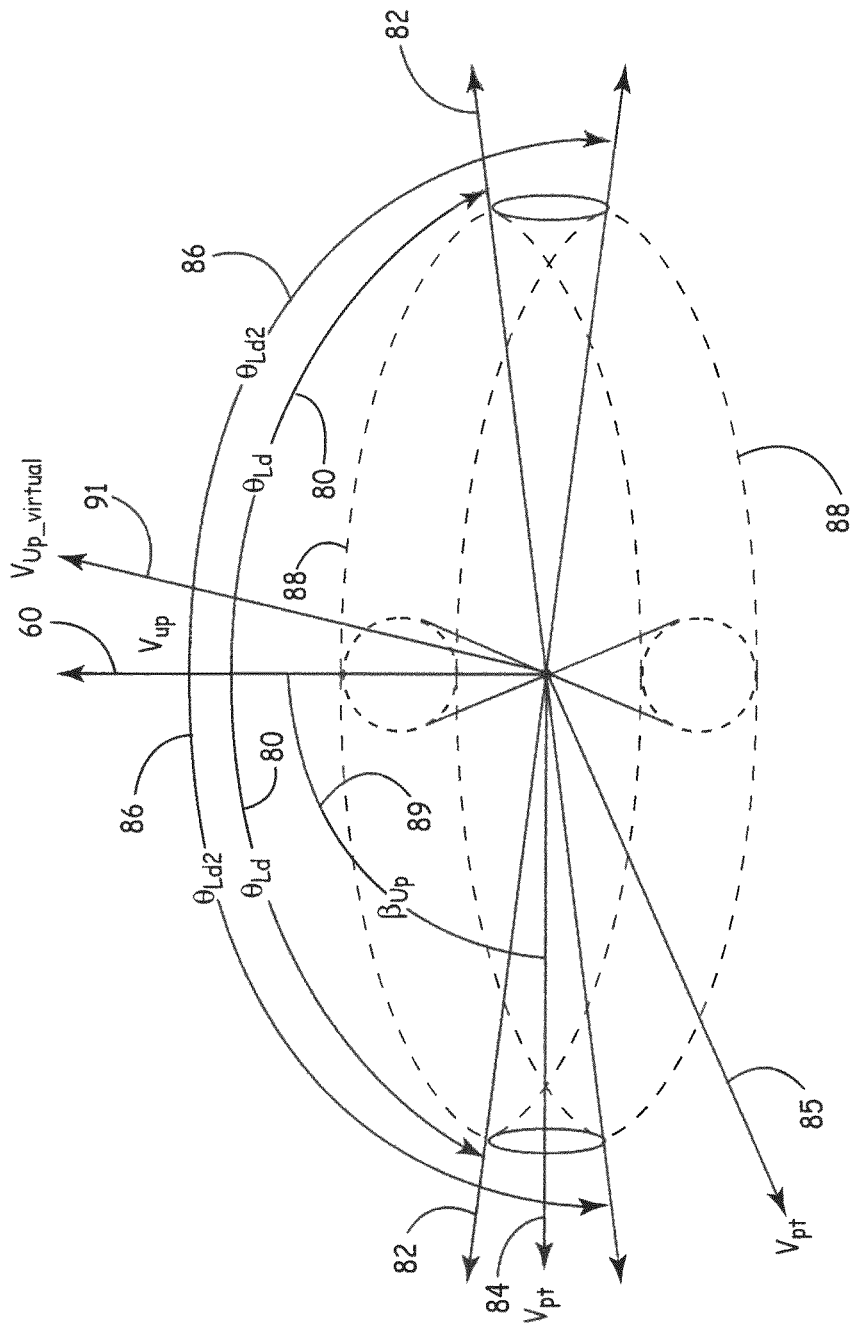
FIG. 5B is a graph illustrating another method of posture definition.

FIG. 5B is a graph illustrating another relationship that may be used to create posture definitions. A posture may be defined using vector $V_{Up}$ 60 and an angle $\theta_{Ld}$ 80 that defines a minimum (rather than a maximum) distance from vector $V_{Up}$ 60. A patient may be classified as occupying this posture if the detected posture vector is farther away from the defined posture vector $V_{Up}$ 60 than the angle $\theta_{Ld}$ 80 (i.e., lies outside of a cone 82). This type of definition may be used to define a Lying Down posture, for instance. According to this example, both of detected posture vectors $V_{pt}$ 84 and $V_{pt}$ 85 will be classified as being in this Lying Down posture since both vectors are outside of cone 82 that surrounds $V_{Up}$ 60.

In yet another example of a posture definition, two angles, $\theta_{Ld}$ 80 and $\theta_{Ld2}$ 86, may be used in conjunction with the defined posture vector $V_{Up}$ 60 to express a tolerance. For example, these two angles may be selected to describe a toroid 88 (shown dashed) that surrounds the posture vector $V_{Up}$. A patient may be classified as occupying the defined posture if the detected posture vector lies within this toroid. In this case, a patient associated with detected posture vector $V_{pt}$ 84 is classified as being in the Lying Down posture since this posture vector lies within toroid 88. However, a patient associated with vector $V_{pt}$ 85 is not classified as being in the Lying Down posture, since this detected posture vector is outside of toroid 88.

As yet another example, multiple vectors and multiple tolerances may be referenced in a single posture definition. For instance, two defined posture vectors, each being associated with respective tolerances, may describe two cones in three dimensional space. These cones may both be used to define a posture. That is, a posture definition may specify that the area within either one, or both, of the cones is included in the definition. This corresponds to an OR-type logic function (e.g., such as a Boolean Logic function). As another example, the definition may specify that only an area that resides in both of two overlapping cones in included in the definition. This corresponds to an AND-type logic function. Another illustration involves specifying that only the area in one, but not the other, of two overlapping cones is included in the definition. This type of operation utilizes both AND- and NOT-type logical functions.

According to another embodiment, a definition may reference one or more toroids and/or one or more cones. These regions may, or may not, overlap. A posture definition may be created that references multiple ones of these regions, and that may further utilize logic functions (e.g., OR, AND, NOT, etc.) to indicate which portions of these regions are to be associated with a particular posture definition. Thus, it will be understood multiple regions in space may be referenced by a single posture definition. When multiple regions are involved, any logic function (e.g., of a Boolean type, etc.) known in the art may be used to define relationships indicating which portions of which regions are included in the posture definitions. Techniques for creating posture definitions using multiple regions in three-dimensional space are described in commonly-assigned patent application entitled "Posture State Classification for a Medical Device" filed on even date herewith and referenced above.

In yet another embodiment, virtual defined posture vectors such a $V_{Up\_virtual}$ 91 of FIG. 5B may be used to create posture definitions. A virtual defined posture vector is a vector that is generated (not measured) by applying processing steps to one or more of the other defined posture vectors. For instance, processing steps (examples of which are described below) may be applied to various defined posture vectors for other postures, such as defined posture vector $V_L$ 66 (FIG. 5A) that is associated with the Left Side posture. These processing steps result in a virtual defined posture vector $V_{Up\_virtual}$ 91. Such virtual defined posture vectors may then be used to classify a patient's posture in a manner that may, in some circumstances, provide advantages over use of other defined posture vectors. This is discussed below in reference to FIG. 9.

Figure 6:
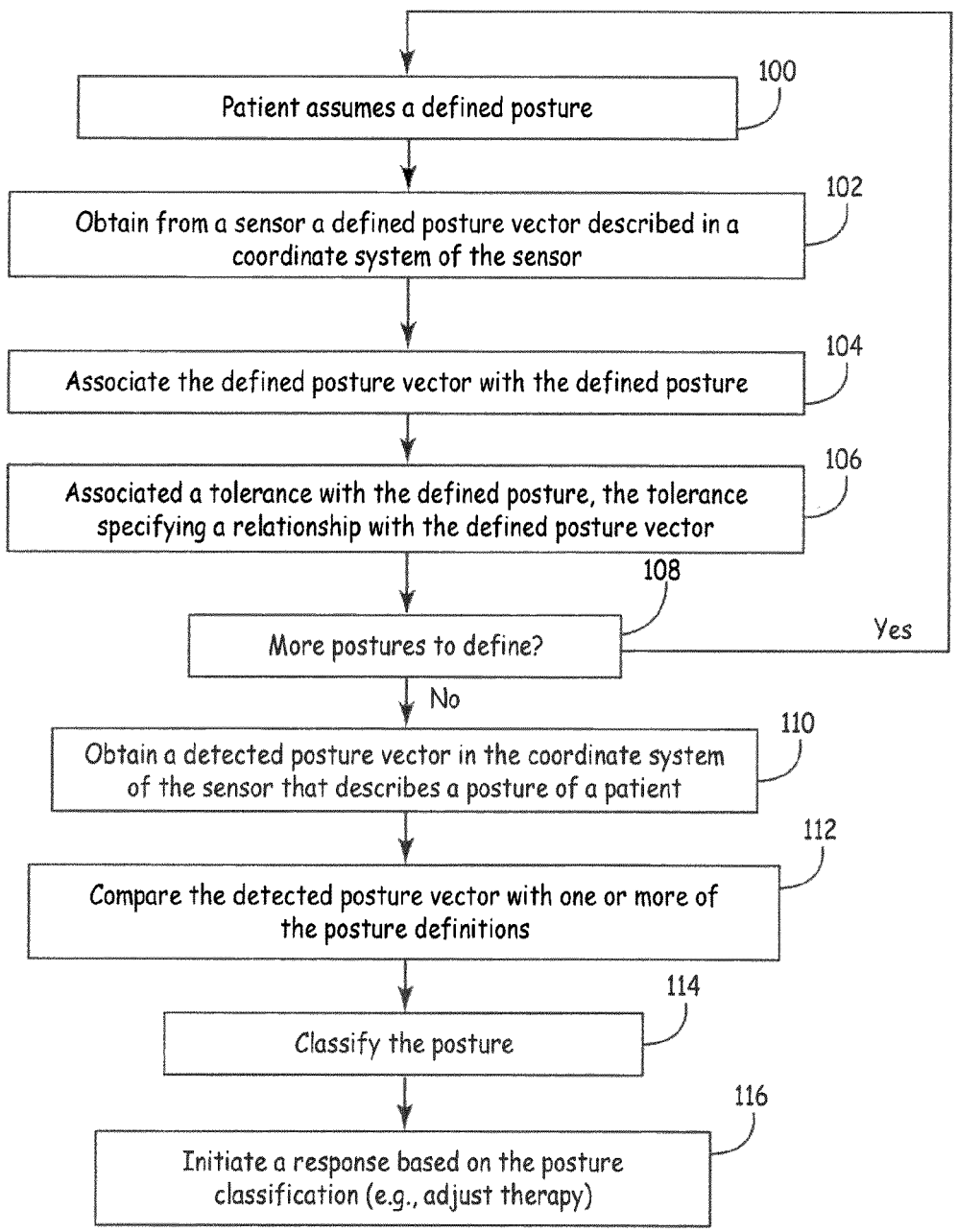
FIG. 6 is a flow diagram describing one method of creating and using posture definitions according to the current disclosure.

FIG. 6 is a flow diagram describing one method of defining posture definitions and using these definitions to classify a patient's posture according to one embodiment of the current disclosure. First, a patient is directed to assume a posture (100). This may be any posture whatsoever. While the patient assumes this posture, a defined posture vector is obtained from sensor 40 that is described in a coordinate system of the sensor (102). The defined posture vector is associated with a defined posture (104). This may be accomplished by storing an indication of the defined posture along with an indication of the defined posture vector, for example.

A tolerance is also associated with the defined posture (106). This tolerance specifies a relationship with the defined posture vector. This relationship may be expressed in terms of one or more regions in space (e.g., cone(s), toroid(s), etc.) positioned relative to a defined posture vector. The regions may be described in multiple ways, as will be discussed further below. Mechanisms for describing these regions may include use of angles, a straight-line distance, a city-block distance, a mathematical relationship such as one that involves trigonometric functions or inner products, and so on. The relationship may further involve a minimum (e.g., "falls within"), a maximum (e.g., "falls outside of"), and/or some type of logic function (e.g., Boolean logic). The association of the tolerance may be accomplished by storing the tolerance along with the indication of the defined posture. If any more postures are to be defined (108), the definition process is repeated by returning to step 100.

After one or more postures are defined in the foregoing manner, processing continues to step 110, where a detected posture vector describing a current posture of a patient is obtained. This detected posture vector is obtained from sensor 40 in the coordinate system of the sensor. The detected posture vector is compare with one or more of the posture definitions to determine whether this detected posture vector has a specified relationship with a defined posture vector as set forth by any of the posture definitions (112). The patient's posture is then classified based on this determination (114). Some response may be initiated based on this posture classification, such as to adjust therapy, provide a notification, or to take some other action (116).

It may be noted that in some embodiments wherein posture definitions overlap, the patient's posture may meet the relationship requirements of more than one defined posture in step 112. In this case, the patient's posture may be classified in step 114 using multiple posture definitions or instead, using a selected one of the posture definitions. This will be discussed further below in reference to posture sub-classifications.

It is possible that the detected posture vector does not have a specified relationship with any of the defined postures in step 112. In this case, the posture may be recorded as Undefined and the desired actions associated with the Undefined posture classification may be initiated. In another embodiment, when this occurs, the posture classification in which the patient was last classified is retained. That is, the patient's most recent posture classification remains unchanged and hysteresis is injected into the system.

The above description focuses on mechanisms for defining and classifying a posture using a coordinate system of the sensor. In particular, this mechanism includes defining postures using the coordinate system of the sensor, obtaining a detected posture vector in the coordinate system of the system, and directly comparing the two vectors to classify the patient's posture. Because a direct comparison is performed without the need to transform, or in any way convert, either of the two vectors into a body coordinate system, processing may be completed more efficiently than when a body coordinate system is referenced. This mechanism may be applied to postures as well as to activity states that are described using vectors, as will be discussed below in reference to classification of activity states.

Next, more specific techniques for comparing detected posture vectors to defined posture vectors are discussed. One way to accomplish this involves comparing angles. For instance, the determination as to whether $V_{pt}$ 84 (FIG. 5B) lies within toroid 88 may be based on a comparison between $\theta_{Ld}$ 80, $\theta_{Ld2}$ 86 and $\theta_{pt}$ 89. Specifically, if $\theta_{Ld}80<\theta_{pt}89<\theta_{Ld2}86$, the patient may be classified in the Lying Down posture according to the definition illustrated in FIG. 5B. To perform this type of classification, however, the angle between $V_{pt}$ 84 and $V_{Up}$ must first be determined, a step that is highly processing intensive, which may require a large expenditure of other system resources (e.g., memory, as when look-up tables are used during this process), and/or which requires a relatively large power expenditure. This is not advantageous, particularly when implantable devices are being used to perform the classification.

An alternative to the foregoing relates to referencing non-angular values referred to herein as similarity values (or simply "similarities"). A similarity is a value that indicates how similar two vectors are to one another without the use of angles. As an example, some type of scalar (non-angular) distance such as a maximum straight-line distance between vectors may be used as a similarity. Other examples include a "city-block" distance, a Euclidean distance, an absolute difference, a Minkowski (p-norm) distance, an inner product, or some other mathematical relationship that compares the two vectors. In one particular embodiment, a cosine or another trigonometric function (sine) is used as a similarity. When similarities rather than angles are used to perform posture classification, posture classification may be completed with relatively few processing steps because no derivation of the angle between the detected posture vector and another vector is needed. This saves a significant amount of power and allows processing to complete faster, as is illustrated in the remaining drawings.

Figure 7A:
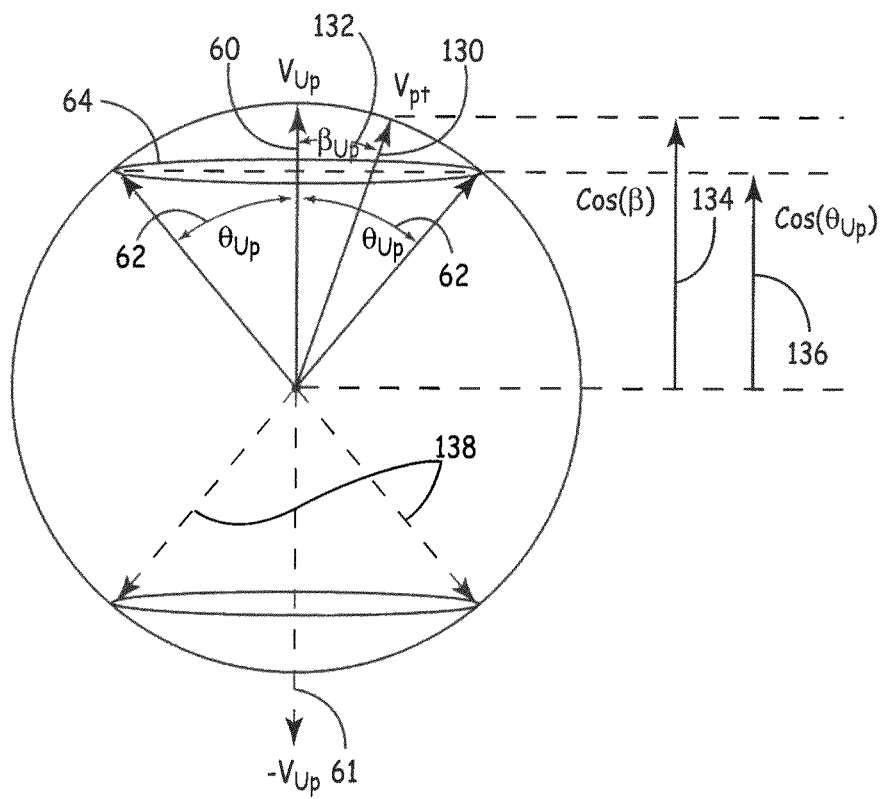
FIG. 7A is a graphical depiction of a posture definition for the Upright posture.

FIG. 7A is a graphical depiction of a posture definition for the Upright posture. This posture is defined in terms of vector $V_{Up}$ 60 and a tolerance that may reference angle $\theta_{Up}$ 62. As previously described in reference to FIGS. 5A and 5B, the angle $\theta_{Up}$ may be used to describe a cone 64 disposed in relationship to vector $V_{Up}$. In this example, a patient's posture will be classified as being Upright if the detected posture vector $V_{pt}$ 130 for the patient lies within cone 64.

As an alternative to referencing angle $\theta_{Up}$ 62, the tolerance may instead be expressed using the cosine of angle $\theta_{Up}$ 62 as well as the cosine of $\beta_{Up}$ 132, where $\beta_{Up}$ is the angle between a detected posture vector $V_{pt}$ 130 and $V_{Up}$ 60, as follows:

$$\text{If } \cos(\beta_{Up}) \geq \cos(\theta_{Up}), \text{Posture=Upright} \quad \text{(Equation 1)}$$

This relationship is depicted by FIG. 7A, which shows the cosine of the angle $\beta_{Up}$ 132 via arrow 134. The cosine of the angle $\theta_{Up}$ is designated by arrow 136. In this case, $\cos(\beta_{Up})$ is greater than $\cos(\theta_{Up})$. Therefore, the patient will be classified as being in the Upright posture.

As may be appreciated by considering Equation 1, the angle of $\theta_{Up}$ is a selected value, and $\cos(\theta_{Up})$ is therefore a predetermined constant that may be determined once after the angle has been selected. The $\cos(\beta_{Up})$ is a similarity value that may be determined after the detected posture vector is obtained, and without ever deriving a value for $\beta_{Up}$. That is, this similarity value may be obtained simply by knowing the detected posture vector and the defined posture vector $V_{Up}$. As a result, the relationship of Equation 1 may be evaluated without angle deriving any angles, thereby significantly simplifying processing operations. This is highly beneficial for applications that are power-limited, such as IMDs that utilize rechargeable batteries.

FIG. 7A further includes a second cone 138 that may be described as a mirror image of cone 130. This second cone 138 is disposed about a vector $-V_{Up}$ 61, which is 180 degrees from vector $V_{Up}$ 60. The use of cone 138 will be discussed further below.

Figure 7B:
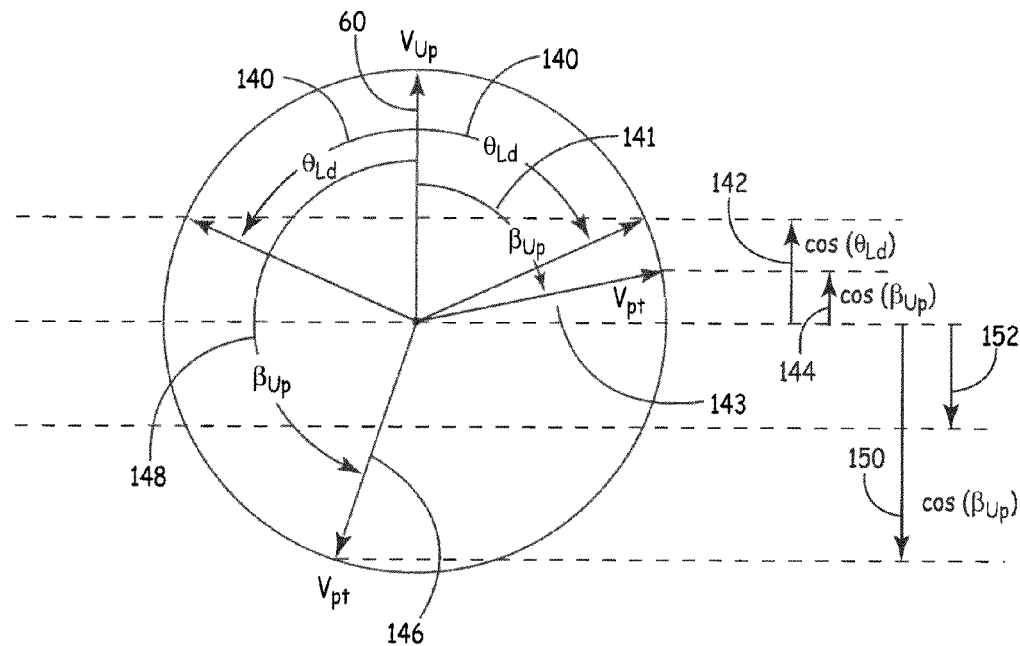
FIG. 7B is a graphical depiction of a posture definition for a Lying Down posture.

FIG. 7B is a graphical depiction of a posture definition for a Lying Down posture such as that already discussed in reference to FIG. 5B above. As previously discussed, the patient may be defined as being in the Lying Down posture whenever a detected posture vector $V_{pt}$ 143 is outside of the cone 64 that surrounds vector $V_{Up}$ 60. Using a cosine as a similarity value, this tolerance relationship may be expressed as follows:

If $\cos(\beta_{Up}) \leq \cos(\theta_{Ld})$, Posture=Lying Down    (Equation 2)

As discussed above, angle $\beta_{Up}$ is the angle between the defined posture vector $V_{Up}$ and the detected posture vector $V_{pt}$ 143.

In the current example, the foregoing relationship is satisfied. The cosine of the angle $\beta_{Up}$ is represented by arrow 144, and the cosine of angle $\theta_{Ld}$ 140 is represented by arrow 142. It may be seen that the cosine of the angle $\beta_{Up}$ 144 is less than the cosine of angle $\theta_{Ld}$ 142 such that a patient having the detected posture vector $V_{pt}$ 143 will be classified as being in the Lying Down posture.

Next, assume the detected posture vector shown as $V_{pt}$ 146 is obtained. Using the foregoing relationship of Equation 2, this detected posture vector will likewise be classified as Lying Down. This will be true even though posture vector $V_{pt}$ 146 may be more aptly categorized as being associated with an inverted position. This posture classification will occur because the angle $\beta_{Up}$ 148 between $V_{pt}$ 146 and $V_{Up}$ 60 has a cosine represented by arrow 150 that is less than the cosine 142 of angle $\theta_{Ld}$. It may be desirable to exclude such posture vectors from a Lying Down definition. To accomplish this, the following tolerance relationship may instead be used to define the Lying Down posture:

If $|\cos(\beta_{Up})| \leq \cos(\theta_{Ld})$, Posture=Lying Down    (Equation 3)

This excludes all vectors for which the cosine of the angle between the detected posture vector and $V_{Up}$ is less than the negative of the cosine of angle $\theta_{Ld}$. Thus, the minimum allowable cosine that satisfies the relationship of Equation 3 is represented by arrow 152.

As was the case described above in regards to FIG. 7A, the current techniques of using similarities such as a cosine to define tolerances allows posture classification to occur in a manner that eliminates the need to determine angles. This is highly advantageous in an application wherein it is desirable to conserve power, as is the case with IMD applications.

Figure 8:
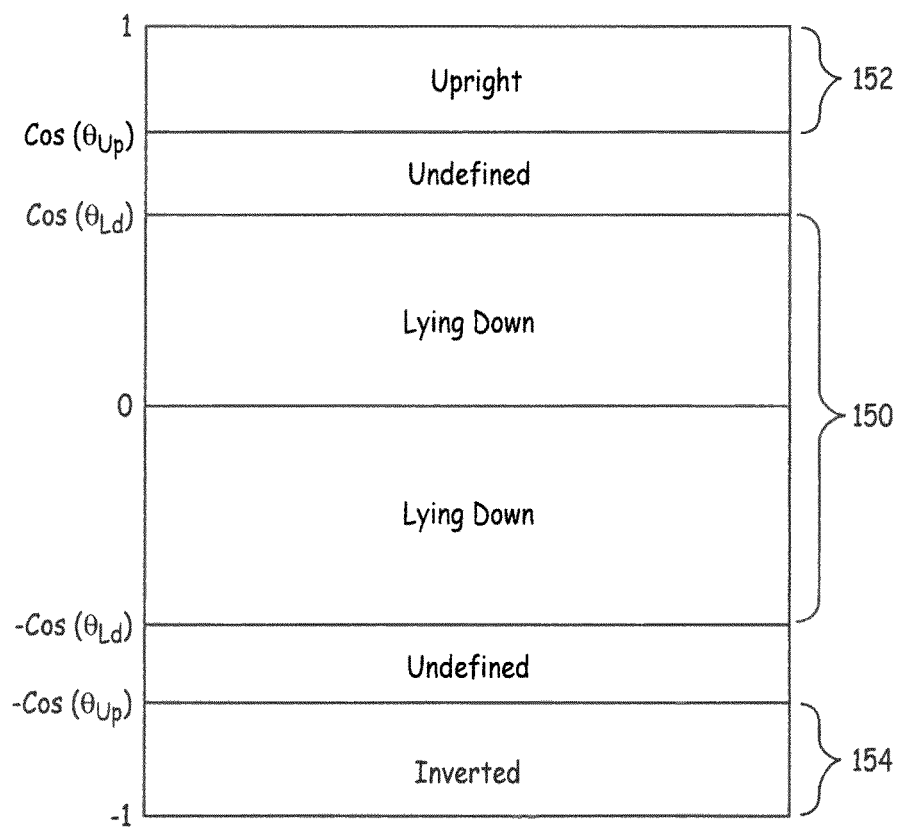
FIG. 8 is a graph that summarizes the exemplary postures and relationships described in relation to FIGS. 7A and 7B.

FIG. 8 is a graph that summarizes the exemplary postures and relationships described above in regards to FIGS. 7A and 7B. The posture Lying Down will be detected if the cosine of the angle between the detected posture vector and the defined posture vector $V_{Up}$ is within a region 150 determined by the pre-selected value $\cos(\theta_{Ld})$. Similarly, the Upright posture will be detected if the cosine of the angle between the detected posture vector and the defined posture vector $V_{Up}$ is within region 152 as determined by the pre-selected value $\cos(\theta_{Up})$. Also shown is another posture, Inverted, which is detected if the cosine of the angle between the detected posture vector and the defined posture vector $V_{Up}$ is within region 154 as determined by the negative of the pre-selected value $\cos(\theta_{Up})$. This latter posture corresponds to one that is "opposite" the Upright posture. For instance, a patient may be classified in this posture if a detected posture vector occupies cone 138 of FIG. 7A.

More or fewer postures may be detected in a manner similar to that described in regards to FIG. 8. For instance, a Leaning posture may be defined. A detected posture vector may be categorized as being associated with this Leaning posture if the detected posture vector falls within a toroid surrounding vector $V_{Up}$ that is defined by a first angle $\theta_{L1}$ and a second $\theta_{L2}$. For instance, angles $\theta_{L1}$ and $\theta_{L2}$ may be 30° and 40°, respectively. Thus, postures may be defined to occupy any one or more regions on the graph of FIG. 8, and the foregoing examples are illustrative only.

Also shown in FIG. 8 are regions 156 and 158, which may be associated with an Undefined posture. If the cosine of the angle between the detected posture vector $V_{pt}$ and the defined posture vector $V_{Up}$ falls into one of these regions, the posture is classified as Undefined. In this case, several alternative embodiments are possible as discussed in relation to FIG. 6 above. In one instance, the patient's posture may simply be classified as Undefined. Alternatively, the patient may be classified as remaining in the last derived posture classification that was anything other than Undefined. That is, the patient's posture classification will remain unchanged, adding hysteresis to the system.

In any of the foregoing ways shown in FIGS. 7A, 7B, and 8, a single defined posture vector such as $V_{Up}$ may be used to create multiple posture definitions. While three defined postures are shown being associated with the same defined posture vector in FIG. 8, many more postures may be associated with this same vector, if desired.

Figure 9:
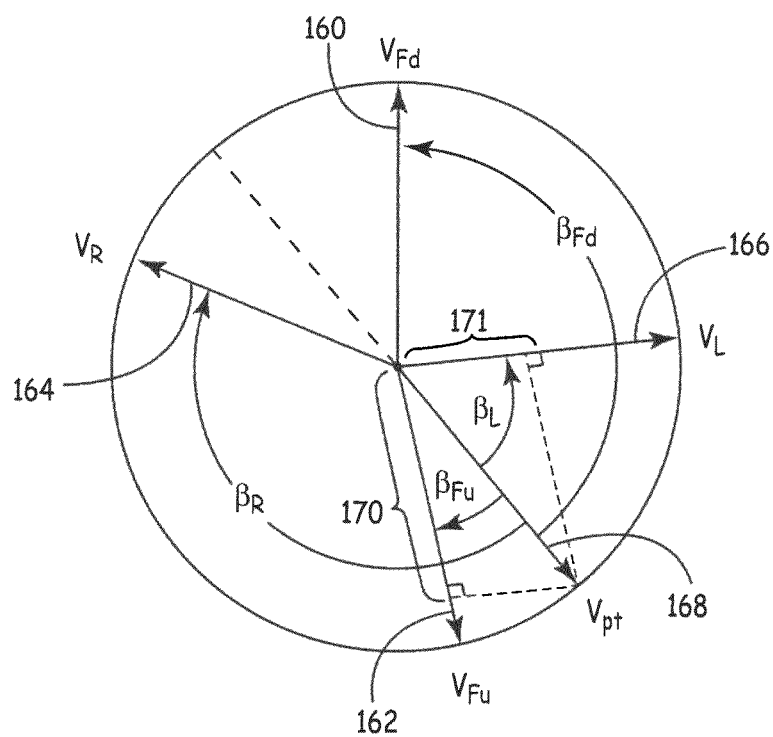
FIG. 9 is graphical depiction of exemplary posture definitions related to postures that a patient may assume when lying down.

FIG. 9 is graphical depiction of posture definitions for multiple postures that a patient may assume when lying down. In one embodiment, this graph may occupy a plane in which the A-P 58c and L-M 58b axes of the patient resides (FIG. 4), but this need not be the case.

Postures occupied by a patient when lying down may include a Face Up posture when the patient is on his back, a Face Down posture assumed when the patient is lying on his stomach, a Right Side posture when the patient is on his right side, and a Left Side posture when the patient is on his left side. In this example, these postures are each associated with defined posture vectors $V_{Fu}$ 162, $V_{Fd}$ 160, $V_R$ 164, and $V_L$ 166, respectively. These vectors are shown as being co-planar in this example, but this need not be the case. Moreover, as shown in FIG. 9, the vectors need not be equidistant from one another, but may be anywhere within three-dimensional space.

In this example, a detected posture vector is represented by $V_{pt}$ 168. This vector forms a respective angle with each of the four vectors $V_{Fd}$ 160, $V_{Fu}$ 162, $V_R$ 164, and $V_L$ 166. These angles are shown as $\beta_{Fd}$, $\beta_{Fu}$, $\beta_R$ and $\beta_L$, respectively. The cosines of each of these angles may be calculated. The patient may be classified as being in whichever posture is associated with the greatest cosine.

In the current example, the cosines for angles $\beta_{Fu}$ and $\beta_L$ are positive numbers, whereas the cosines for angles $\beta_R$ and $\beta_{Fd}$ are negative numbers (since these two angles are between 90 and 270 degrees). Of the two positive cosines, the cosine for angle $\beta_{Fu}$, which is represented by line segment 170, is larger than the cosine for angle $\beta_L$, which is represented by line segment 171. Thus, the largest cosine is that associated with angle $\beta_{Fu}$ corresponding to the Face Up posture. Therefore, according to this tolerance relationship, the patient will be classified as being in the Face Up posture.

According to the method of FIG. 9, the tolerance relationship may be described as "largest of the cosines of angles $\beta_{Fd}$, $\beta_{Fu}$, $\beta_R$ and $\beta_L$". This provides a very efficient manner to classify a patient in one of any number of lying down postures using cosines. No angle derivations are needed, saving power and processing time. Moreover, the processing may be further simplified through the use of inner products. This will be described further below.

It will be noted that more or fewer lying down postures may be defined, and the use of four lying down postures in FIG. 9 is merely illustrative. The foregoing method may be applied regardless of the number of defined posture vectors in use. The cosine of the angle between the detected posture vector and each of the N defined posture vectors may be determined, with the largest cosine being that associated with the defined posture vector to be used to classify the patient's posture.

Figure 10A:
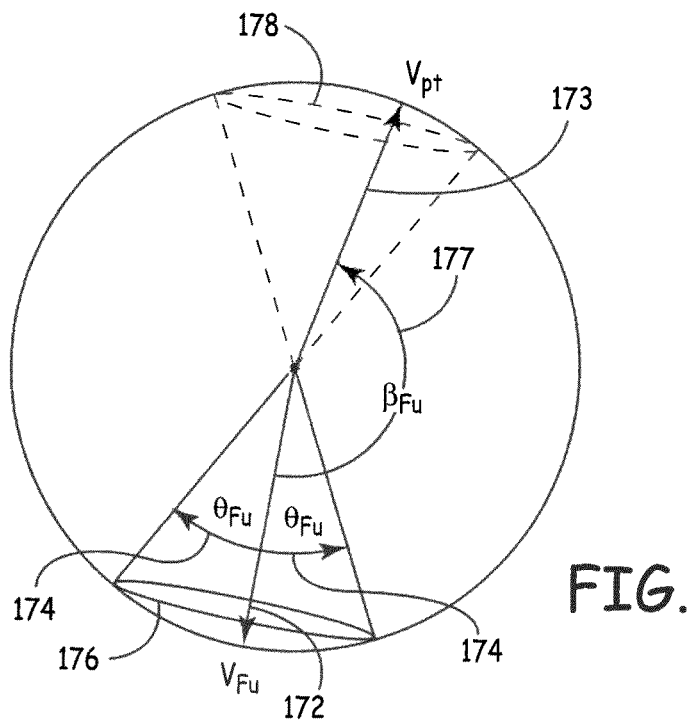
FIG. 10A is an alternative graphical depiction of exemplary posture definitions related to postures that a patient may assume when lying down.

FIG. 10A is an alternative graphical depiction of posture definitions for multiple postures that a patient may assume when lying down. This depiction, like that of FIG. 9, includes a defined posture vector $V_{Fu}$ 172 that is used to define a Face Up posture. Unlike the embodiment of FIG. 9 which classifies postures by selecting the largest of the cosines of $\beta_{Fd}$, $\beta_{Fu}$, $\beta_R$ and $\beta_L$, this alternative method is similar to that shown in FIG. 7A which bases posture classification on cones. A determination is made as to whether the detected posture vector $V_{pt}$ 173 is within a cone 176 surrounding vector $V_{Fu}$, wherein the size of the cone is defined by the cosine of angle $\theta_{Fu}$ 174. If the detected posture vector is within this cone, the patient may be classified as being in the Face Up posture. To determine whether $V_{pt}$ 173 is within a cone 176, the cosine of the angle $\beta_{Fu}$ 177 between the detected posture vector $V_{pt}$ 173 and the vector $V_{Fu}$ 172 is compared to the cosine of angle $\theta_{Fu}$. If the cosine of the angle $\beta_{Fu}$ is greater than the cosine of angle $\theta_{Fu}$, the detected posture vector is within cone 176, and the patient will be determined to be in the Face Up posture.

In the embodiment of FIG. 10A, the same defined posture vector $V_{Fu}$ 172 and angle $\theta_{Fu}$ 174 that are used to define the Face Up posture are also used to define the Face Down posture. In this case, however, it is determined whether the cosine of the angle $\beta_{Fu}$ 177 between the detected posture vector $V_{pt}$ 173 and $V_{Fu}$ 172 is less than the negative cosine of angle $\theta_{Fu}$. When this relationship is satisfied, the detected posture vector $V_{pt}$ 173 lies within cone 178 (shown dashed), and will be determined to correspond to the Face Down posture. This is the case in the instant example. In this manner, a Face Down posture is defined to be the exact "opposite" of the Face Up vector in much the way the Inverted posture of FIG. 7A (related to cone 138) is the opposite of the Upright posture associated with cone 64. Of course, in another embodiment, such postures need not be defined as being "opposites", as is discussed below.

Figure 10B:
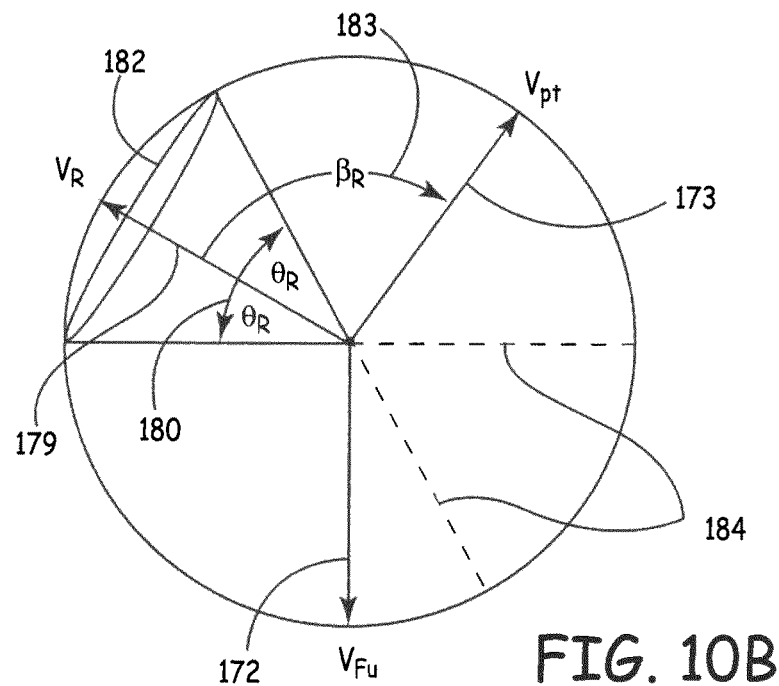
FIG. 10B is another graphical depiction of exemplary posture definitions.

Next, FIG. 10B is considered. FIG. 10B is a graphical depiction of posture definitions that includes $V_{Fu}$, and also includes an additional defined posture vector $V_R$ 179 that is used to define the Right Side posture. This posture definition also includes a tolerance that will reference the pre-selected angle $\theta_R$ 180, which describes a cone 182 surrounding the vector $V_R$. If the detected posture vector is within this cone, the patient is determined to be in the posture Right Side. As was the case in the preceding examples, this determination may be made using the cosine of the angle $\beta_R$ 183, which is the angle between the detected posture vector $V_{pt}$ 173 and the vector $V_R$ 179. In particular, it is determined whether the cosine of the angle $\beta_R$ is greater than the cosine of angle $\theta_R$. If so, the detected posture vector is within cone 182, and the patient will be determined to be in the Right Side posture. In this example, the cosine of the angle $\beta_R$ 183 is not greater than the cosine of angle $\theta_R$ 180 and the detected posture vector $V_{pt}$ 173 will not be classified as being associated with the Right Side posture.

As was the case with the Face Up and Face Down postures, in this example, the Left Side posture is defined to be the "opposite" of the Right Side posture. To determine whether the patient is on his Left Side, it is determined whether the cosine of the angle $\beta_R$ 183 between the detected posture vector $V_{pt}$ and $V_R$ is less than the negative cosine of angle $\theta_R$. When this is true, the detected posture vector lies within cone 184 (shown dashed), and will be determined to correspond to the Left Side posture.

Several comparisons may be drawn between the embodiment of FIG. 9 and that of FIGS. 10A and 10B. FIGS. 10A and 10B utilize postures that are "opposites" of other postures. For instance, the Right Side posture may be thought of as an opposite of the Left Side posture. As a result, fewer defined posture vectors and angles need be selected in this alternative embodiment. This is not the case in the embodiment of FIG. 9, which does not require, for example, the Right Side and the Left Side to be opposites. Thus, FIG. 9 may be somewhat more flexible.

As another observation, the embodiment of FIG. 9 does not contemplate any Undefined posture space, since the detected posture vector will be classified as being in the posture associated with the defined posture vector to which it is closest. In contrast, the embodiment of FIGS. 10A and 10B may result in a detected posture vector falling outside of any defined posture. In this case, it is possible for a posture to be classified as Undefined.

In yet another embodiment that is a hybrid of the embodiments shown in FIGS. 9, 10A and 10B, respective defined posture vectors may be selected in the manner shown in FIG. 9 for each of the posture definitions. That is, there may be four vectors selected for each of the four lying down postures that are exemplified, each being defined independently of the others. Such posture vectors need not be opposites of each other. A respective tolerance may then be selected to define cones for each posture definition. Each tolerance may be different (e.g., a different size cone) from those selected for any other posture. In this manner, each posture definition is associated with a cone of any size that may be unique for that posture, and the postures need not be opposites of any other posture.

In any of the aforementioned embodiments involving posture classification, processing is carried out without the need to calculate any angles. The only angles that are used in these calculations are the pre-selected values assigned at the time postures are defined (e.g., $\theta_{Fu}$, $\theta_{Fd}$, etc.). No angle derivation is performed during the classification steps, greatly simplifying processing and saving power in power-limited environments such as those existing in an IMD.

Next, more specific processing steps are considered in regards to comparing a detected posture vector $V_{pt}$ to a defined posture vector. For the following examples, cosines are used for this comparison. This need not be the case, however, as will be discussed further below.

For the following description, assume the detected posture vector, $V_{pt}$, is represented as the vector:

$$V_{pt} = [V_{pt1} V_{pt2} V_{pt3}] \quad \text{(Equation 4)}$$

A defined posture vector may be represented generally as the vector:

$$V = [V_1 V_2 V_3] \quad \text{(Equation 5)}$$

The cosine of an angle β between the detected posture vector and the defined posture vector may be described as:

$$\cos(\beta) = \frac{V_1 \cdot V_{pt1} + V_2 \cdot V_{pt2} + V_3 \cdot V_{pt3}}{\sqrt{V_1^2 + V_2^2 + V_3^2} \cdot \sqrt{V_{pt1}^2 + V_{pt2}^2 + V_{pt3}^2}} \quad \text{(Equation 6)}$$

The vector $V_{Up}$ associated with the Upright posture may be expressed as:

$$V_{Up} = [V_{Up1}, V_{Up2}, V_{Up3}] \quad \text{(Equation 7)}$$

Thus, the cosine of the angle $\beta_{Up}$ between $V_{Up}$ and the detected posture vector $V_{pt}$ may be described as follows:

$$\cos(\beta_{Up}) = \frac{V_{pt1} \cdot V_{Up1} + V_{pt2} \cdot V_{Up2} + V_{pt3} \cdot V_{Up3}}{\sqrt{V_{Up1}^2 + V_{Up2}^2 + V_{Up3}^2} \cdot \sqrt{V_{pt1}^2 + V_{pt2}^2 + V_{pt3}^2}} \quad \text{(Equation 8)}$$

Next, assume that in the manner previously described in reference to Equation 1, the tolerance for the Upright posture is described as:

$$\text{If } \cos(\beta_{Up}) \geq \cos(\theta_{Up}), \text{Posture=Upright} \quad \text{(Equation 9)}$$

Substituting Equation 8 into Equation 9, squaring both sides, and then multiplying both sides by $(V_{Up1}^2 + V_{Up2}^2 + V_{Up3}^2) \cdot (V_{pt1}^2 + V_{pt2}^2 + V_{pt3}^2)$ yields the following:

$$(V_{pt1} \cdot V_{Up1} + V_{pt2} \cdot V_{Up2} + V_{pt3} V_{Up3})^2 \geq \cos^2(\theta_{Up}) \cdot (V_{Up1}^2 + V_{Up2}^2 + V_{Up3}^2) \cdot (V_{pt1}^2 + V_{pt2}^2 + V_{pt3}^2) \quad \text{(Equation 10)}$$

As may be appreciated, this relationship applies to the Upright posture so long as the inner product of $V_{pt}$ and $V_{Up}$ is greater than zero. That is, this relationship applies to the Upright posture so long as the following is true:

$$(V_{pt1} \cdot V_{Up1} + V_{pt2} \cdot V_{Up2} + V_{pt3} \cdot V_{Up3}) > 0 \quad \text{(Equation 11)}$$

If the inner product appearing on the left side of Equation 11 is instead less than zero, the detected posture vector $V_{pt}$ and the Upright posture vector $V_{Up}$ form an angle that is between 90 and 270 degrees such that the two angles are dissimilar, rather than being similar. In this case, the patient's posture is "opposite" the Upright posture, which is the Inverted posture.

It may be noted that a portion of Equation 10 is a constant, which may be referred to as $\Delta_{Up}^2$ as follows:

$$\Delta_{Up}^2 = \cos^2(\theta_{Up}) \cdot (V_{Up1}^2 + V_{Up2}^2 + V_{Up3}^2) \quad \text{(Equation 12)}$$

For a vector $V = [V_1, V_2, V_3]$, the term $V_1^2 + V_2^2 + V_3^2$ may be referred to as the "squared length" of the vector. Thus, $\Delta_{Up}^2$ is the product of $\cos^2(\theta_{Up})$ and the squared length of the vector $V_{Up}$. The value for $\Delta_{Up}^2$ need be determined only once after $V_{Up}$ and $\theta_{Up}$ have been selected. This simplifies processing.

According to one embodiment of the disclosure, a further simplification may be achieved that involves normalization of the defined posture vectors. When all defined posture vectors are normalized, the squared length appearing in Equation 12 will be the same value for all defined posture vectors.

To normalize a defined posture vector such as $V_{Up} = [V_{Up1}, V_{Up2}, V_{Up3}]$, each of the x, y, and z components of this vector are divided by the length $\|V_{Up}\|$ of the vector and multiplied by a scale factor S, as follows:

$$\text{Norm}(V_{Up}) = \frac{[V_{Up1}, V_{Up2}, V_{Up3}]}{\|V_{Up}\|} \times S \text{ where} \quad \text{(Equation 13)}$$

$$\|V_{Up}\| = \sqrt{V_{Up1}^2 + V_{Up2}^2 + V_{Up3}^2}$$

In this equation, S is any selected scale factor that may be programmable or hard-coded. In one case, S may be selected to be a value such as 1, 10 or 100 for ease of computation. When this normalization process is performed for each defined posture vector, the squared length $(V_{Up1}^2 + V_{Up2}^2 + V_{Up3}^2)$ will always be equal to $S^2$.

As previously described in reference to Equation 12, after $V_{Up}$ and $\theta_{Up}$ are known, the constant $\Delta_{Up}^2$ may be determined for the Upright posture as $\Delta_{Up}^2 = \cos^2(\theta_{Up}) \cdot (V_{Up1}^2 + V_{Up2}^2 + V_{Up3}^2)$, wherein $(V_{Up1}^2 + V_{Up2}^2 + V_{Up3}^2) = S^2$ in an embodiment utilizing normalization. This computation may be performed once, and thereafter need not be repeated so long as $\theta_{Up}$ and $V_{Up}$ do not change. The value for $\Delta_{Up}^2$ may be stored along with the Upright posture definition in the posture state definitions 52 of FIG. 3, or may be retained in another manner. The constant $\Delta_{Up}^2$ may be used to perform posture detection as follows:

$$\text{IF } (V_{pt1} \cdot V_{Up1} + V_{pt2} \cdot V_{Up2} + V_{pt3} \cdot V_{Up3})^2 \geq \Delta^2_{Up} \cdot (V_{pt1}^2 + V_{pt2}^2 + V_{pt3}^2) \text{ AND } (V_{pt1} \cdot V_{Up1} + V_{pt2} \cdot V_{Up2} + V_{pt3} \cdot V_{Up3}) > 0 \text{ THEN Posture=Upright} \quad \text{(Equation 14)}$$

As may be appreciated, use of the constant $\Delta^2_{Up}$ reduces the number of processing steps that must be performed to detect a posture. After obtaining the detected posture vector, $V_{pt} = [V_{pt1}, V_{pt2}, V_{pt3}]$, very few processing steps are required to determine whether the detected posture vector falls within the tolerance for the "Upright" posture definition. Thus, as described above, no angle derivations are needed. Moreover, any processing-intensive steps (e.g., derivation of square roots) have been eliminated. This is advantageous when seeking to conserve power in an application adapted for use in an IMD.

The steps discussed above in reference to the Upright posture may be applied to the definition for the Lying Down posture that appears in reference to Equation 2. This will yield a similar expanded relationship for the Lying Down posture that may be expressed as follows:

$$\text{IF } (V_{pt1} \cdot V_{Up1} + V_{pt2} \cdot V_{Up2} + V_{pt3} \cdot V_{Up3})^2 \leq \Delta^2_{Ld} \cdot (V_{pt1}^2 + V_{pt2}^2 + V_{pt3}^2) \text{ where } \Delta^2_{Ld} = \cos^2(\theta_{Ld}) \cdot (V_{Up1}^2 + V_{Up2}^2 + V_{Up3}^2) \text{ THEN Posture=Lying Down} \quad \text{(Equation 15)}$$

In a manner similar to that described above, $\Delta_{Ld}^2$ is a constant, the value of which may be determined after definition of the Lying Down posture is complete such that $V_{Up}$ and $\theta_{Ld}$ have been selected. As previously described, in one embodiment, the definition of this defined posture will involve normalization of the defined posture vector so that this vector has the same length as all other defined posture vectors in use within the system.

As yet another example, an Inverted posture may be defined using the following equation:

$$\text{IF } (V_{pt1} \cdot V_{Up1} + V_{pt2} \cdot V_{Up2} + V_{pt3} \cdot V_{Up3})^2 \geq \Delta^2_{Up} \cdot (V_{pt1}^2 + V_{pt2}^2 + V_{pt3}^2) \text{ AND } (V_{pt1} \cdot V_{Up1} + V_{pt2} \cdot V_{Up2} + V_{pt3} \cdot V_{Up3}) < 0 \text{ THEN Posture=Inverted} \quad \text{(Equation 16)}$$

Equation 16 is similar to Equation 14 which describes the Upright posture. However, for the Inverted posture, the inner product between $V_{pt}$ and $V_{Up}$ is negative. This Inverted posture may be thought of as the "opposite" of the Upright Posture. For instance, to be classified as being in the Inverted posture, the vector $V_{pt}$ lies within cone 138 of FIG. 7A, which is the "opposite" of cone 64 defining the Upright posture.

As previously described, $\Delta^2_{Up}$ is a constant that can be determined once in the aforementioned manner and saved along with the definition for the Inverted posture so that this portion of the processing steps need not be repeated during posture classification. Moreover, since Equation 14 and 16 describe "opposite" postures, once processing is performed to determine whether the posture is Upright, no further processing is needed to determine whether the patient is in the Inverted posture. The values derived from Equation 14 need merely be substituted into Equation 16 to obtain the result. This even further simplifies processing.

The processing steps described above in reference to the Lying Down, Upright, and Inverted postures may be adapted for use in classifying a patient in one of N lying down postures such as Face Up, Face Down, Right Side, and Left Side. As an example, the Face Up and Face Down postures are defined in FIG. 10A using the pre-selected angle $\theta_{Fu}$. Classification of the detected posture vector $V_{pt}$ may occur by determining the cosine of an angle $\beta$ between the detected posture vector $V_{pt}$ and a defined posture vector such as $V_{Fu}$ and comparing this determined cosine to that of a corresponding cosine of pre-selected angle $\theta_{Fu}$ as follows:

$$\text{If } \cos(\beta_{Fu}) \geq \cos(\theta_{Fu}), \text{Posture=Face Up} \quad \text{(Equation 17)}$$

where $\beta_{Fu}$ is the angle between the detected posture vector $V_{pt}$ and the defined posture vector $V_{Fu}$. Applying processing steps that are similar to those discussed above, the relationship of Equation 17 may be expressed in expanded terms as follows:

$$\text{IF } (V_{pt1} \cdot V_{Fu1} + V_{pt2} \cdot V_{Fu2} + V_{pt3} \cdot V_{Fu3})^2 \geq \Delta^2_{Fu}(V_{pt1}^2 + V_{pt2}^2 + V_{pt3}^2) \text{ AND } (V_{pt1} \cdot V_{Fu1} + V_{pt2} \cdot V_{Fu2} + V_{pt3} \cdot V_{Fu3}) > 0 \text{ THEN Posture=Face Up} \quad \text{(Equation 18)}$$

In a manner similar to that described above, $\Delta^2_{Fu}$ is a constant described as follows:

$$\Delta^2_{Fu} = \cos^2(\theta_{Fu}) \cdot (V_{Fu1}^2 + V_{Fu2}^2 + V_{Fu3}^2) \quad \text{(Equation 19)}$$

This constant may be derived once after the selection of $V_{Fu}$ and $\theta_{Fu}$ and thereafter will not change until the Face Up posture is redefined. This constant value may be stored along with the posture definition, if desired. If normalized defined posture vectors are in use within the system, this constant will always have the same known value of $\cos^2(\theta_{Fu}) \cdot S^2$, where $S^2$ is the same for every defined posture vector.

The "opposite" posture, Face Down, may be described using the following relationship, as was discussed in regards to FIG. 10A above:

$$\text{If } \cos(\theta_{Fu}) < -\cos(\theta_{Fu}), \text{Posture=Face Down} \quad \text{(Equation 20)}$$

This relationship describes cone 178 of FIG. 10A. If the detected posture vector satisfies this relationship, the patient is in the Face Down posture. This relationship may be expanded in a manner similar to that described above, as follows:

$$\text{IF } (V_{pt1} \cdot V_{Fu1} + V_{pt2} \cdot V_{Fu2} + V_{pt3} \cdot V_{Fu3})^2 \geq \Delta^2_{Fu}(V_{pt1}^2 + V_{pt2}^2 + V_{pt3}^2) \text{ AND } (V_{pt1} \cdot V_{Fu1} + V_{pt2} \cdot V_{Fu2} + V_{pt3} \cdot V_{Fu3}) < 0 \text{ THEN Posture=Face Down} \quad \text{(Equation 21)}$$

Since the Face Up and Face Down are "opposite" postures, once processing is performed to determine whether the posture is Face Up according to Equation 18, no further computational steps are required to determine whether the posture is Face Down. The values derived in regards to Equation 17 may be merely substituted into Equation 21 to obtain the result. This even further simplifies processing.

A similar set of definitions may be defined for the postures Right Side and Left Side shown in FIG. 10B. For instance, the tolerance for the posture Right Side may be expressed as follows:

$$\text{If } \cos(\beta_R) \geq \cos(\theta_R), \text{Posture=Right Side} \quad \text{(Equation 22)}$$

wherein $\beta_R$ is the angle between the detected posture vector and $V_R$. This relationship may be expanded as follows:

$$\text{IF } (V_{pt1} \cdot V_{R1} + V_{pt2} \cdot V_{R2} + V_{pt3} \cdot V_{R3})^2 \geq \Delta^2_R \cdot (V_{pt1}^2 + V_{pt2}^2 + V_{pt3}^2) \text{ AND } (V_{pt1} \cdot V_{R1} + V_{pt2} \cdot V_{R2} + V_{pt3} \cdot V_{R3}) > 0 \text{ THEN Posture=Right Side} \quad \text{(Equation 23)}$$

As was the case above, $\Delta^2_R$ is a constant described as follows:

$$\Delta^2_R = \cos^2(\theta_R) \cdot (V_{R1}^2 + V_{R2}^2 + V_{R3}^2) \quad \text{(Equation 24)}$$

This constant may be derived once after the selection of $V_R$ and $\theta_R$ and thereafter will not change until the Right Side posture is redefined. As previously discussed, the squared length will be a constant $S^2$ in an embodiment utilizing normalization.

Similarly, a posture Left Side may be expressed as follows:

$$\text{If } \cos(\beta_R) < -\cos(\theta_R), \text{Posture=Left Side} \quad \text{(Equation 25)}$$

$$\text{IF } (V_{pt1} \cdot V_{R1} + V_{pt2} \cdot V_{R2} + V_{pt3} \cdot V_{R3})^2 \geq \Delta^2_R \cdot (V_{pt1}^2 + V_{pt2}^2 + V_{pt3}^2) \text{ AND } (V_{pt1} \cdot V_{R1} + V_{pt2} \cdot V_{R2} + V_{pt3} \cdot V_{R3}) < 0 \text{ THEN Posture=Left Side} \quad \text{(Equation 26)}$$

Since the Right Side and Left Side are "opposite" postures, once processing is performed to determine whether the posture is Right Side per Equation 23, no further computational steps are required to determine whether the posture is Left Side. The values derived in regards to Equation 23 may be merely substituted into Equation 26 to obtain the result.

The discussion involving the processing steps that may be used to perform posture classification according to examples of FIGS. 10A and 10B assume that certain postures (e.g., Face Up and Face Down, Right Side and Left Side) will be "opposites" of one another. As previously described, this need not be the case. For instance, the Face Up and Face Down postures need not have any relationship to one another, and indeed need not even be co-planar. This is likewise true of the Right Side and Left Side postures. In such an embodiment, each such posture may be defined using a respective defined posture vector and a respective tolerance that is independent of any of the other posture definitions. In such cases, posture classification will occur for each posture in the manner shown above for the Face Up and Right Side postures (e.g., see Equations 18 and 23, respectively) without the types of simplifications afforded by assuming "opposites", as shown in Equations 21 and 26, for example.

The above description involving Equations 4-26 relates to exemplary processing steps that may be used during posture classification to complete vector processing without the need to derive angles and so that processing steps are minimized. That discussion focused on embodiments that compare the detected posture vector $V_{pt}$ to cones surrounding defined posture vectors. This is as shown in FIGS. 7A, 7B, 10A and 10B, for example. As previously described, alternative embodiments may perform posture classification by comparing $V_{pt}$ to each of multiple defined posture vectors to determine to which defined posture vector the detected posture vector $V_{pt}$ is closest. This alternative approach is shown in reference to FIG. 9. The following discussion describes how the specific processing steps set forth above in regards to a cone-based approach may be adapted for use with a method of the type shown in FIG. 9.

Returning to FIG. 9, recall that a detected posture vector $V_{pt}$ 168 is used to form a respective angle $\beta$ with each of four posture vectors $V_{Fu}$, $V_{Fd}$, $V_L$, and $V_R$. It is then determined which of the four angles has the largest cosine. The defined posture vector resulting in the largest cosine will be used to classify the posture.

The specific processing steps used to determine the largest cosine may be performed using Equation 8 set forth above. For instance, the cosine of the angle $\beta_{Fu}$ between the defined posture vector $V_{Fu}$ and $V_{pt}$ is expressed follows:

$$\cos(\beta_{Fu}) = \frac{V_{pt1} \cdot V_{Fu1} + V_{pt2} \cdot V_{Fu2} + V_{pt3} \cdot V_{Fu3}}{\sqrt{V_{Fu1}^2 + V_{Fu2}^2 + V_{Fu3}^2} \cdot \sqrt{V_{pt1}^2 + V_{pt2}^2 + V_{pt3}^2}} \quad \text{(Equation 27)}$$

A similar equation may be solved for each of the cosines of the other angles $\beta_{Fd}$, $\beta_R$, $\beta_L$ for each of the lying down postures exemplified in FIG. 9 to determine the largest cosine.

The processing associated with Equation 27 involves the use of square root operations, which is processing intensive and/or may require a large expenditure of other system resources. To eliminate the requirement to perform square root calculations, the squared cosine value, rather than the cosine value, may be derived instead. For instance, in the case of the Face Up vector, square of the cosine is as follows:

$$\cos^2(\beta_{Fu}) = \frac{(V_{pt1} \cdot V_{Fu1} + V_{pt2} \cdot V_{Fu2} + V_{pt3} \cdot V_{Fu3})^2}{(V_{Fu1}^2 + V_{Fu2}^2 + V_{Fu3}^2) \cdot (V_{pt1}^2 + V_{pt2}^2 + V_{pt3}^2)} \quad \text{(Equation 28)}$$

This equation may be used to determine which of the squared cosine values is the largest and also provides a positive inner product, wherein the inner product is defined as:

$$\text{Inner Product} = V_{pt1} \cdot V_1 + V_{pt2} \cdot V_2 + V_{pt3} \cdot V_3 \quad \text{(Equation 29)}$$

The defined posture vector that meets these requirements will be the closest to the detected posture vector and will be used to classify the posture.

One way to streamline the above approach is to determine the inner product between the detected posture vector $V_{pt}$ and each of the defined posture vectors before determining a cosine or squared cosine value. If the inner product is negative, it indicates the angle between the detected posture vector $V_{pt}$ and the defined posture vector V lies between 90 and 270 degrees (that is, the detected posture vector is in a direction that is at least somewhat "opposite" to the defined posture vector). In this case, the defined posture vector resulting in the negative inner product may be disregarded for posture classification purposes. Only the defined posture vectors that yield a position inner product with the detected posture vectors need be processed any further to determine either a cosine or squared cosine value in the manner described above.

Processing may be even further streamlined by recognizing that the first term of the denominator of Equation 28 is the squared length of the defined posture vector. As noted above, this squared length is a constant that may be pre-determined once the defined posture vector is known. This constant may be stored along with the posture definition for use during posture classification operations.

Recall that if normalized defined posture vectors are in use within the system, the squared length will be a constant that has the same known value of $S^2$ for every defined posture vector, and therefore in this type of system, this value need not be stored. In this case, comparisons between any two squared cosine values for any two defined postures is simplified even further because the lengths of two defined posture vectors are always the same, and therefore "cancel out" of the comparison. As an example, the cosine value for the detected posture vector of $V_{Fu}$ for the Face Up posture (Equation 27)

$$\cos(\beta_{Fu}) = \frac{V_{pt1} \cdot V_{Fu1} + V_{pt2} \cdot V_{Fu2} + V_{pt3} \cdot V_{Fu3}}{\sqrt{V_{Fu1}^2 + V_{Fu2}^2 + V_{Fu3}^2} \cdot \sqrt{V_{pt1}^2 + V_{pt2}^2 + V_{pt3}^2}}$$

may be compared to that for the detected posture of $V_R$ for the Right Side posture, as follows:

$$\cos(\beta_R) = \frac{V_{pt1} \cdot V_{R1} + V_{pt2} \cdot V_{R2} + V_{pt3} \cdot V_{R3}}{\sqrt{V_{R1}^2 + V_{R2}^2 + V_{R3}^2} \cdot \sqrt{V_{pt1}^2 + V_{pt2}^2 + V_{pt3}^2}} \quad \text{(Equation 30)}$$

If normalized defined posture vectors are being utilized, the length for $V_{Fu}$ and $V_R$ that appear as the first terms in the denominators of the respective equations each has the same value. Moreover, the length for the detected posture vector $V_{pt}$ appearing as the second term in the denominators will likewise be the same in both equations. This allows the comparison between the two cosine values to be simplified to a determination as to which defined posture vector $V_{Fu}$ and $V_R$ produces the largest inner product with $V_{pt}$. Thus, in this case, the similarity value is simplified to just the inner product.

The foregoing mechanism provides a very efficient approach for determining to which of N defined posture vectors a detected posture vector is closest. In the example of FIG. 9, this approach is used to classify a detected posture vector with respect to N postures assumed by a patient who is lying down. In another embodiment, this approach may be generalized to categorize a patient's posture with respect to any set of defined posture vectors in three-dimensional space. If all such defined posture vectors have been normalized in the above-described manner, whichever defined posture vector in the set that results in the largest inner product with $V_{pt}$ may be determined to be closest to $V_{pt}$. Moreover, it will be understood that any of the techniques described herein may be applied to other postures instead of, or in addition to, those discussed above. Any posture in three-dimensional space may be defined and used according to the current disclosure.

In the above examples, posture classification is occurring using similarities between a detected posture vector $V_{pt}$ and each of one or more defined posture vectors that involve either cosines of angles, or in a simplified version, inner products. However, other similarities may be used. For instance, a sine, rather than a cosine, may be employed for this purpose. In a particular example, a "smallest sine" relationship may be utilized rather than a "largest cosine" relationship to determine a closest defined posture vector to a detected posture vector. As another example, a city-block distance $d(V, V_{pt})$ may be derived between a detected posture vector $V_{pt} = [V_{pt1} \; V_{pt2} \; V_{pt3}]$ and a defined posture vector $V = [V_1 \; V_2 \; V_3]$ as follows:

$$d(V, V_{pt}) = |V_1 - V_{pt1}| + |V_2 - V_{pt2}| + |V_3 - V_{pt3}| \quad \text{(Equation 31)}$$

A variation of this technique provides a Euclidean distance as follows:

$$d(V, V_{pt}) = \sqrt{(V_1 - V_{pt1})^2 + (V_2 - V_{pt2})^2 + (V_3 - V_{pt3})^2} \quad \text{(Equation 32)}$$

Yet another technique utilizes a maximum absolute difference $d_\infty (V, V_{pt})$ as follows:

$$d_\infty(V,V_{pt})=\max\{|V_1-V_{pt1}|,|V_2-V_{pt2}|,|V_3-V_{pt3}|\} \quad \text{(Equation 33)}$$

As another example, a Minkowski (P-Norm) distance may be used. Other mechanisms may be used to describe a similarity between two vectors that does not involve the calculation of an angle.

The alternative types of similarities may be used to define a posture in any of the ways described above. That is, a posture definition may be created that includes a defined posture vector and a tolerance. The tolerance describes a relationship that references one or more similarities of any of the types described herein. During use, a detected posture vector is obtained from a patient and compared to a defined posture vector to obtain a similarity that is preferably of the type referenced by the posture definitions so that a meaningful comparison may be performed. If this similarity fulfills the relationship specified by the tolerance, the patient is classified as being in the defined posture.

As may be appreciated, the types of distance relationships discussed above, as well as certain trigonometric functions (e.g., sine of angles) generate similarity values having an inverse relationship to the degree of similarity existing between the two vectors that are being compared. For example, in the case of distance relationships, a similarity value of 0 indicates the two vectors are the same (that is, they possess the highest degree of similarity possible with respect to one another). In these cases, it may be desirable to use a function that maps this original similarity value (represented as σ) to a value ranging between 0 and some maximum value $\sigma_{max}$, wherein a value of "0" indicates a "least similar" relationship between the two vectors that are being compared and the maximum value indicates a "most similar" relationship between the two vectors. That is, this function maps the original similarity to a new value ω that is directly proportional to degree of similarity between the two compared vectors.

One type of mapping function may involve subtracting the original similarity value σ from "one" (e.g., as may be useful in the case of the sine of an angle). The function may instead involve subtracting the similarity value σ from some other maximum possible similarity value $\sigma_{max}$ and then dividing by $\sigma_{max}$ to obtain the new similarity value ω. This is represented as follows:

$$\omega = \frac{\sigma_{max} - \sigma}{\sigma_{max}} \quad \text{(Equation 34)}$$

This function maps an original similarity value of 0 to 1, and an original similarity value of $\sigma_{max}$ to 0.

Another type of function that may be used for this purpose is as follows:

$$\omega = \frac{1}{1+\sigma^2} \quad \text{(Equation 35)}$$

Still another example involves the following:

$$\omega = e^{-\lambda\sigma} \quad \text{(Equation 36)}$$

In Equation 36, constant λ is selected to determine the rate of decay. Like Equation 34, both of Equations 35 and 36 map the original similarity value σ to a value ranging between 0 and 1, with the new value ω of 0 representing a "least similar" relationship between two vectors that are being compared and a value of 1 indicating a "most similar" relationship between the vectors.

According to an alternative approach, "fuzzy" logic may be employed to map a similarity to a new value ω as described in relation to FIGS. 11A-11E.

FIGS. 11A-11E are exemplary embodiments of functions for converting similarity values σ to new values ω when the original similarity values σ are inversely proportional to the degree of similarity between two vectors that are being compared. In such cases, the original similarity values (shown along the x axis) range between 0 and ∞. The new value ω, shown along the y axis, will be the largest when the similarity value is 0, indicating the two vectors being compared are substantially the same. In each of the examples of FIGS. 11A-11E, the new values ω diminish to 0 at some predetermined similarity value which may be different for each of the graphs.

Figure 11A:
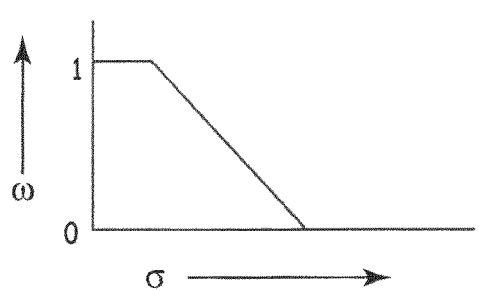
FIGS. 11A-11E are graphs of functions for mapping a similarity value to a new value for use in performing posture classification.
Figure 11B:
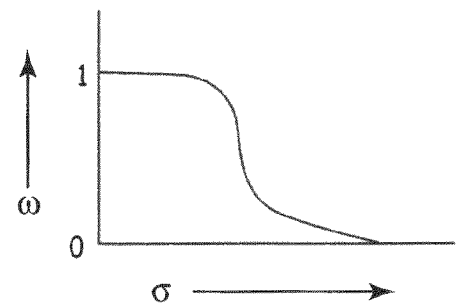
Figure 11C:
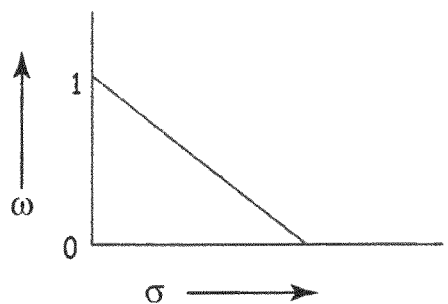
Figure 11D:
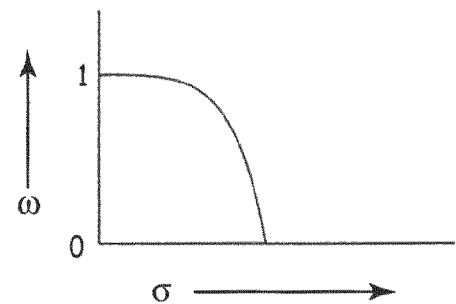
Figure 11E:
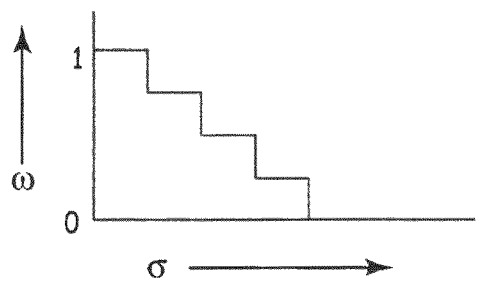

A virtually limitless number of relationships may be used to map an original similarity value σ to a new value ω. For instance, FIGS. 11A and 11D utilize various non-linear relationships. In FIGS. 11B and 11E, step-like functions are employed. In FIG. 11C, a linear relationship is used. It will be appreciated that the various functions shown in FIGS. 11A-11E, are merely exemplary. In one embodiment, the function that is in use at any given time within the system may be selected by a user such as a clinician using a programming interface, as may be provided via programmer 20. This function may alternatively be pre-selected by the device manufacturer. In another embodiment, a default function is selected by the device manufacturer, with the user being allowed to override this default using a programming interface.

After mapping an original similarity value to obtain a value ω, this new value may be used according to any of the techniques described above. That is, the new value ω may be used to create a posture definition that references a defined posture vector and a tolerance, with the tolerance being described in terms of the new value ω. During use of this type of posture definition, a detected posture vector is obtained from a patient and compared to a defined posture vector to obtain a similarity that is then mapped to a new value according to the foregoing discussion. This new value is compared to a posture definition to determine whether the relationship specified by the tolerance is satisfied. If so, the patient is classified as being in the defined posture.

The foregoing discussion focuses on creating and using posture definitions that reference a defined posture vector. In one embodiment, a defined posture vector is obtained as a patient assumes a defined posture. Because this defined posture vector corresponds to an actual posture that the patient assumes, this type of vector may be considered an "actual" defined posture vector. As mentioned above in reference to FIG. 5B, another type of defined posture vector that may be referenced by a posture definition is "virtual" rather than "actual". A virtual defined posture vector (or simply "virtual posture vector") is a vector that may be obtained by applying processing steps to one or more of the other defined posture vectors. This can be appreciated by returning to FIG. 9.

In FIG. 9, each of the cones associated with a prone posture is defined using a corresponding defined posture vector $V_{Fu}$ 162, $V_{Fd}$ 160, $V_R$ 164, and $V_L$ 166. Such vectors may be obtained as the patient assumes the corresponding postures. These four vectors may be used to obtain a virtual posture vector for the Upright posture. This virtual vector may, but need not, correspond to the actual defined posture vector $V_{Up}$ 60 that was obtained when the patient assumed the Upright posture. For instance, as shown in FIG. 5B, a virtual upright posture vector $V_{Up\_virtual}$ 91 may have a same general direction as the actual Upright vector $V_{Up}$, but need not align with $V_{Up}$.

According to one method, a virtual posture vector for the Upright posture is obtained using multiple cross-products. For instance, a cross-product between the vectors for the Face Down and the Left Side postures (that is, $V_{Fd}$ and $V_L$) may be used to derive a vector $V_{Norm1}$ that is perpendicular to both $V_{Fd}$ and $V_L$ and that has a direction determined by the right-hand rule. This direction may correspond somewhat to the S-I axis of the patient and will also be in the same general direction as the defined posture vector $V_{Up}$.

In a similar manner, three additional normal vectors $V_{Norm2}$, $V_{Norm3}$, and $V_{Norm4}$, may be determined for adjacent vector pairs $(V_L, V_{Fu})$, $(V_{Fu}, V_R)$, and $(V_R, V_{Fd})$, respectively, keeping in mind that the cross-product relationship is not commutative. In each case, the resulting vector $V_{Norm2}$, $V_{Norm3}$, and $V_{Norm4}$ is perpendicular to the two vectors used to produce the vector, and will have a direction determined by the right-hand rule. This direction may generally coincide with the S-I axis of the patient.

The four resulting vectors $V_{Norm1}$-$V_{Norm4}$ may then be averaged to obtain virtual Upright vector $V_{Up\_virtual}$. As may be appreciated, in this example, averaging is accomplished by adding the first vector components of each of $V_{Norm1}$-$V_{Norm4}$ (that is, all four of the x-axis components) and dividing by four to obtain the first vector component of $V_{Up\_virtual}$. Similarly, all of the second vector components (that is, all four of the y-axis components) may be averaged to obtain the second vector component of $V_{Up\_virtual}$, and all of the third vector components may be averaged to obtain the third vector component of $V_{Up\_virtual}$.

The resulting virtual posture vector $V_{Up\_virtual}$ may have a direction that is generally perpendicular to a plane that approximates the planes in which the various lying down postures reside, and which may correspond somewhat to the S-I axis of the patient. While the virtual vector will have a same general direction as the defined posture vector $V_{Up}$, the two vectors need not be the same.

A virtual vector such as $V_{Up\_virtual}$ may be advantageously used to perform posture classification, and is particularly useful in detecting Lying Down postures. This is true because some postures that a patient assumes when lying down may involve an incline, such as when the patient's head is "propped up" on a pillow. Thus, the plane that best approximates the multiple planes in which all prone posture vectors lie is likely not a plane that is normal to $V_{Up}$. Therefore, a toroid surrounding $V_{Up}$ may not provide optimal detection of the Lying Down postures. A more sensitive detection will be provided by a definition that references $V_{Up\_virtual}$, and which may further describe a toroid or some other spatial region in reference to this virtual vector.

The above described virtual vector processing techniques may be applied to any number of N postures defined within the system, and is not limited to the four defined postures described above. In one embodiment, each normal vector $V_{Normx}$ is obtained as the cross-product of two adjacent vectors, taking into account that the cross-product is not commutative, and the right-hand rule must be followed. As one example, this may involve obtaining the cross-products while traveling in a counter-clockwise direction around the patient's S-I axis. As another example, this may involve traveling in a clockwise direction, and then using the negative of the average as the virtual posture vector.

In the above example, each of the defined posture vectors $V_{Fu}$, $V_L$, $V_{Fd}$, and $V_R$ used to generate the virtual vector is a defined posture vector obtained by having the patient assume the Face Up, Left Side, Face Down, and Right Side positions in the manner discussed above. However, the concept is not so limited. In another embodiment, a virtual vector may be obtained as an average of the cross-products of other defined vectors that are unrelated to postures the patient assumes while lying down. Moreover, a virtual vector may be obtained using other virtual vectors alone, or in combination with, defined posture vectors. Moreover, the cross-products need not be formed by crossing adjacent vector pairs, but could be obtained using non-adjacent vector pairs in another embodiment.

According to another approach for determining a virtual vector, a plane is located that best approximates the subspace of the vectors being used to obtain the virtual vector. For instance, in this example, a plane is located that best approximates the subspace of the four defined posture vectors $V_{Fu}$, $V_{Fd}$, $V_R$, and $V_L$. This can be done by calculating the two singular dominant vectors that best approximate these four lying down vectors, and then obtaining the cross-product of the two dominant vectors. To accomplish this, a three-by-four matrix $X=[V_{Fu}, V_{Fd}, V_R, V_L]$ is formed that contains each of the defined posture vectors for the four lying down postures. A singular value decomposition may then be used to find the two orthogonal vectors $U_1$ and $U_2$ that best approximates the range of X. A cross-product of $U_1$ and $U_2$ may then be obtained which is in the same general direction as $V_{Up}$. This cross-product may be used as a virtual vector.

In the above-described manner, a virtual vector may be referenced in a posture definition according to any of the techniques described herein. Moreover, this definition may be utilized when classifying a patient's posture according to any of the mechanisms described herein.

The above description provides various types of systems and methods that may be used to streamline posture classification and/or make posture classification more flexible and robust. Yet another type of technique used for this purpose involves evaluating a condition referenced by a posture definition. This may be described by returning to the example of FIG. 7A. In that illustration, the Upright posture is defined in terms of the detected posture vector $V_{Up}$ 60 and a cone 64 surrounding $V_{Up}$ 60. According to that definition, so long as a detected posture vector $V_{pt}$ 130 is anywhere within the cone 64, the posture is classified as Upright. To be classified in association with Upright posture, it does not matter where within the cone 64 that $V_{pt}$ lies, only that $V_{pt}$ is somewhere within this cone.

In some circumstances, it may be advantageous to allow an aspect of the posture definition to be selectable based on evaluation of a condition. For instance, it may be desirable to allow the size of the cone surrounding $V_{Up}$ to be determined based on which side of the defined posture vector $V_{pt}$ lies. Specifically, when a patient is leaning backward, as may occur when the patient is in a reclining chair, it may be advantageous to detect that the patient has exited the Upright posture when the detected posture vector $V_{pt}$ is still relatively close to $V_{Up}$. This would allow a change in therapy to be triggered relatively quickly when the patient leans backwards into a reclining position, thus preventing patient discomfort that may occur if therapy levels associated with the Upright posture are utilized while the patient is leaning backward, as in a reclining chair.

Such considerations are not present when a patient is leaning forward. In fact, it may be desirable to allow the patient to continue to be classified in an Upright position even when the patient is in forward-leaning posture that is relatively far away from the $V_{Up}$ vector. This would allow the patient to continue receiving therapy associated with the Upright posture during such activities as stair climbing that may require the patient to lean forward in a substantial manner. During such activities, it is likely desirable to allow the same therapy associated with the Upright posture to be delivered to the patient.

In accordance with the foregoing example, the size of a cone surrounding $V_{Up}$ may be made selectable based on a condition. In this case, the condition involves determining whether a patient's detected posture vector $V_{pt}$ is closer to a Face Up posture vector $V_{Fu}$ such that the patient is backward leaning, or whether $V_{pt}$ is closer to a Face Down posture vector $V_{Fd}$ such that the patient is more forward leaning. If $V_{pt}$ is determined to be closer to the Face Up posture, a tolerance is selected that causes the patient to exit out of the Upright posture faster than if $V_{pt}$ is closer to the Face Down position. In other words, the cone referenced by the tolerance relationship may be smaller if $V_{pt}$ is determined to be closer to the Face Up posture than it would be if $V_{pt}$ is determined to be closer to the Face Down posture. The "closest to" determination could be made using techniques such as described in reference to FIG. 9. In one embodiment, this determination could be made based on which of the defined posture vectors $V_{Fu}$ or $V_{Fd}$ produces a positive inner product with $V_{pt}$.

According to the current example, $V_{pt}$ is compared to $V_{Fu}$ and $V_{Fd}$ and the results of the comparison are used to select a tolerance angle for use in describing a cone surrounding $V_{Up}$. In other cases, more than two vectors may be involved in the comparison. If desired, $V_{pt}$ 316 may be compared again N posture vectors (e.g., defined posture vectors for the Right Side, Left Side, Face Up, Face Down, etc.), with the result of all N comparisons being used to determine the tolerance. Moreover, the evaluation need not be limited to a two-way outcome. For instance, in this example involving N posture vectors, N or more outcomes may be possible from which to select (e.g., N different cone sizes).

In another embodiment, the condition being evaluated may involve some other type of comparison, such as a comparison involving a system parameter or physiological condition of the patient, rather than defined or virtual posture vectors.

While the exemplary evaluation involved a "closest to" determination for identifying to which of two vectors $V_{pt}$ was closest, this need not be the case. Any other type of relationship may be used when making this determination. For instance, a determination involving which vector is farthest, or which vector falls within some distance range, may be used in the alternative. The relationship may involve some other type of comparison rather than a comparison between two vectors, such as a comparison involving a system parameter or physiological condition of the patient.

Whereas the foregoing example involves selection of a cone size, this need not be the case. In another scenario, a selection of regions may be involved. For instance, a toroid-shaped region in space may be selected for use with a definition based on one outcome, and one or more cones may be selected for use with the definition based on another outcome. The size of these regions, the number of regions, the manner in which the regions are interrelated (e.g., using Boolean logic) may be selected based on evaluation of the condition. This adds further flexibility to the posture definitions.

Next, methods are considered for classifying detected posture vectors using various sets of posture definitions. In one embodiment, a detected posture vector is first classified using the set of posture definitions that includes the Upright, Lying Down, Inverted, or Undefined postures, as shown in FIGS. 7A and 7B. If the patient is determined to be in the Lying Down posture based on this initial classification, further posture classification may occur to classify the patient in a posture that is a sub-classifications of the Lying Down posture. This sub-classification may include Face Up, Face Down, Right Side, and Left Side. In one embodiment, the sub-classifications may further include the Undefined posture. More or fewer Lying Down postures may be used in the alternative. In this manner, a patient's posture may first be classified using a first set of postures, and then further re-classified using sub-classifications of the posture in which the patient was originally classified. Both classification steps may be performed according to any of the techniques described above.

Figure 12:
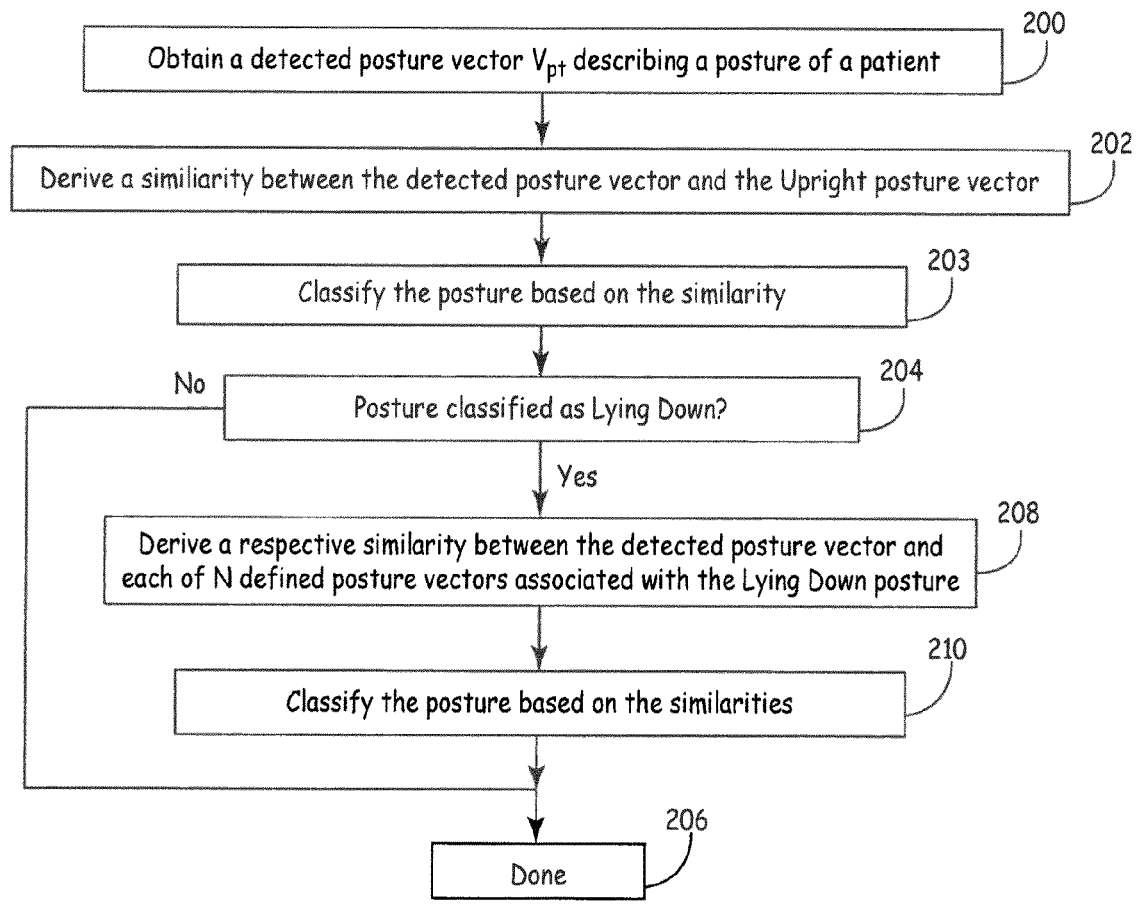
FIG. 12 is a flow diagram illustrating one method of using defined posture vectors to classify a posture according to the current disclosure.

FIG. 12 is a flow diagram illustrating one method of using defined posture vectors to classify a posture according to the current disclosure. The defined posture vectors may be any combination of actual and/or virtual defined posture vectors. First, a detected posture vector may be obtained that describes a current posture of a patient (200). The detected posture vector may be compared to a defined posture vector for an Upright posture to obtain a similarity value (202) and the patient's posture may be classified based on this similarity value (203). This may be accomplished using the techniques described above in reference to FIGS. 7A and 7B, or using any of the other alternative mechanisms described herein. As previously discussed, the similarity is a non-angular value that indicates how similar the vectors are to one another. This similarity may involve trigonometric functions, city-block distances, Euclidean distances, maximum absolute distances, p-norm distances, and the like. In some embodiments, the similarity is an inner product.

If, in step 202, the patient's posture is not classified as the Lying Down posture (204), processing is completed (206). In this case, the patient's posture has been classified as some posture other than Lying Down based on the similarity derived in step 202. This may include the Upright, Inverted or Undefined postures according to one embodiment. In another embodiment, this may further involve one or more leaning postures that are defined with respective to the Upright posture vector.

If, in step 204, the detected posture vector is classified as the Lying Down posture, similarities may be derived between the detected posture vector and each of the N postures associated with the Lying Down posture (208) and the patient's posture may be classified based on these similarities (210). In the example above, this involves comparing the detected posture vector to the defined posture vectors for the Face Up, Face Down, Right Side, and Left Side postures, which are sub-classifications of the Lying Down posture. Processing is then considered complete (206).

While the current examples describe use of sub-classifications only in regards to the Lying Down posture, any other posture may be associated with sub-classifications. In addition, one of the Face Up, Face Down, Right Side or Left Side postures may be further associated with sub-classifications, and so on. This may result in a posture hierarchy that is any number of levels deep, if desired. The flow diagram of FIG. 13 illustrates this type of processing.

Figure 13:
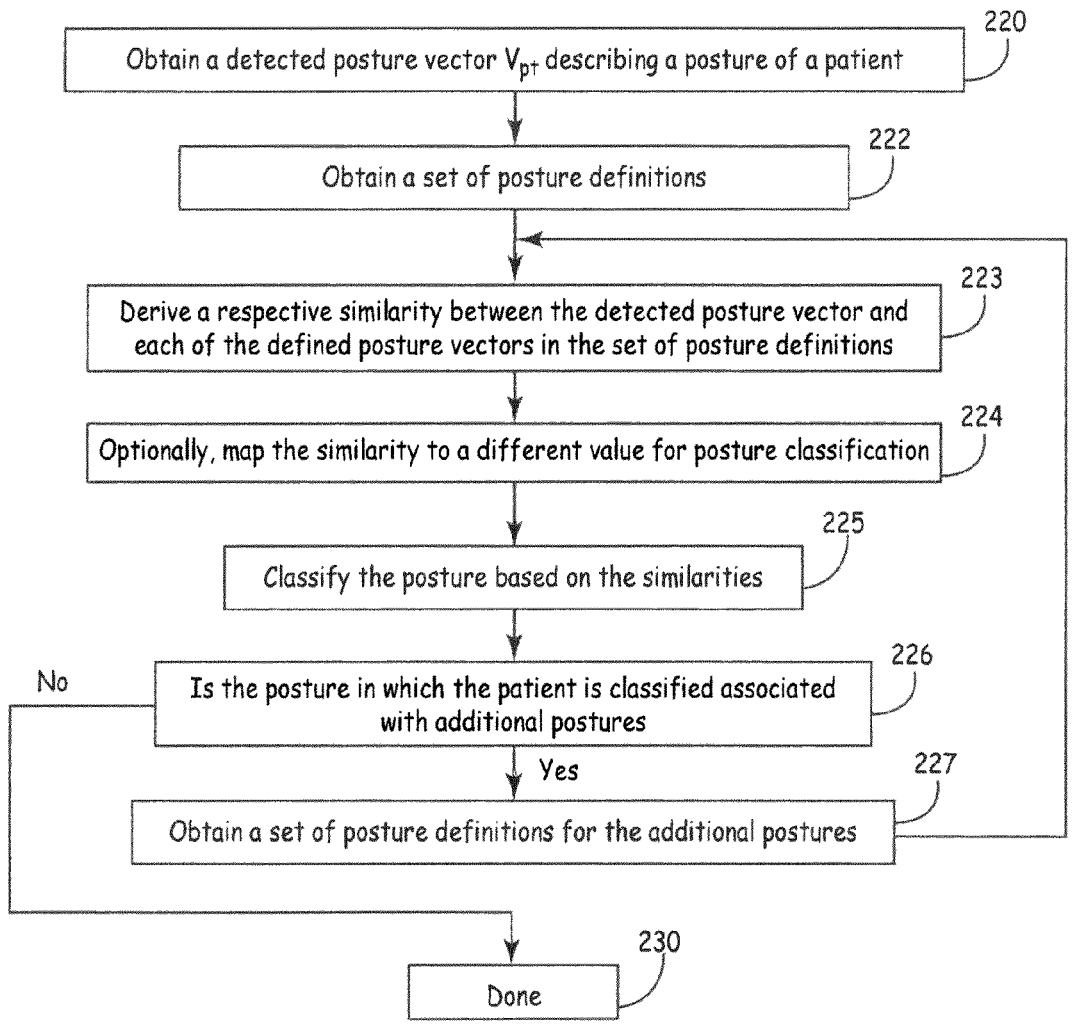
FIG. 13 is a flow diagram of a more generalized method of using defined posture vectors to classify a posture.

FIG. 13 is a flow diagram of a more generalized method of using defined posture vectors to classify a posture. The defined posture vectors may be any combination of actual and/or virtual defined posture vectors. According to this generalized approach, a detected posture vector is obtained from a patient (220). A set of posture definitions is then obtained (222). This set may include any or all of the posture definitions that have been created. For instance, this first set may include the Upright, Lying Down, Inverted, and Undefined postures.

Next, a respective similarity may be derived between the detected posture vector and each of the defined posture vectors in the set of posture definitions (223). Optionally, the similarity may be mapped to a different value that will be used to classifying the patient's posture (224). This may be desirable if an inverse relationship exists between the original similarity values obtained in step 223 and the degree of similarities between the compared vectors. Mapping may be accomplished using a function such as shown in FIGS. 11A-11E or some other function.

The patient's posture may be classified based on the similarities (225). If mapping was performed according to step 224, this classification step may utilize the similarity values ω obtained from this mapping. If the resulting posture classification has sub-classifications (i.e., this posture classification is associated with additional postures) (226), an additional set of postures definitions is obtained (228). For instance, this may involve obtaining the various posture definitions associated with the Lying Down posture, such as Face Up, Face Down, and so on. Thereafter, the process may be repeated by returning to step 224 to re-classify the posture using the additional definitions.

If, in step 226, the current posture classification is not associated with additional posture definitions, the process is completed (230).

In the foregoing manner, the process of FIG. 13 supports hierarchical posture definitions. Processing occurs first for postures at the highest level in the hierarchy (e.g., Lying Down and Upright), and proceeds down the hierarchy to the various sub-classifications (e.g., Face Up, Face Down, etc.). Any number of levels of hierarchy may be included in the posture organization. If desired, all posture definitions may be processed during the same iteration, collapsing the hierarchy into a single level. The embodiment selected may be based on efficiency considerations affected by the number of posture definitions in use in the system at a given time, or some other consideration.

Figure 14:
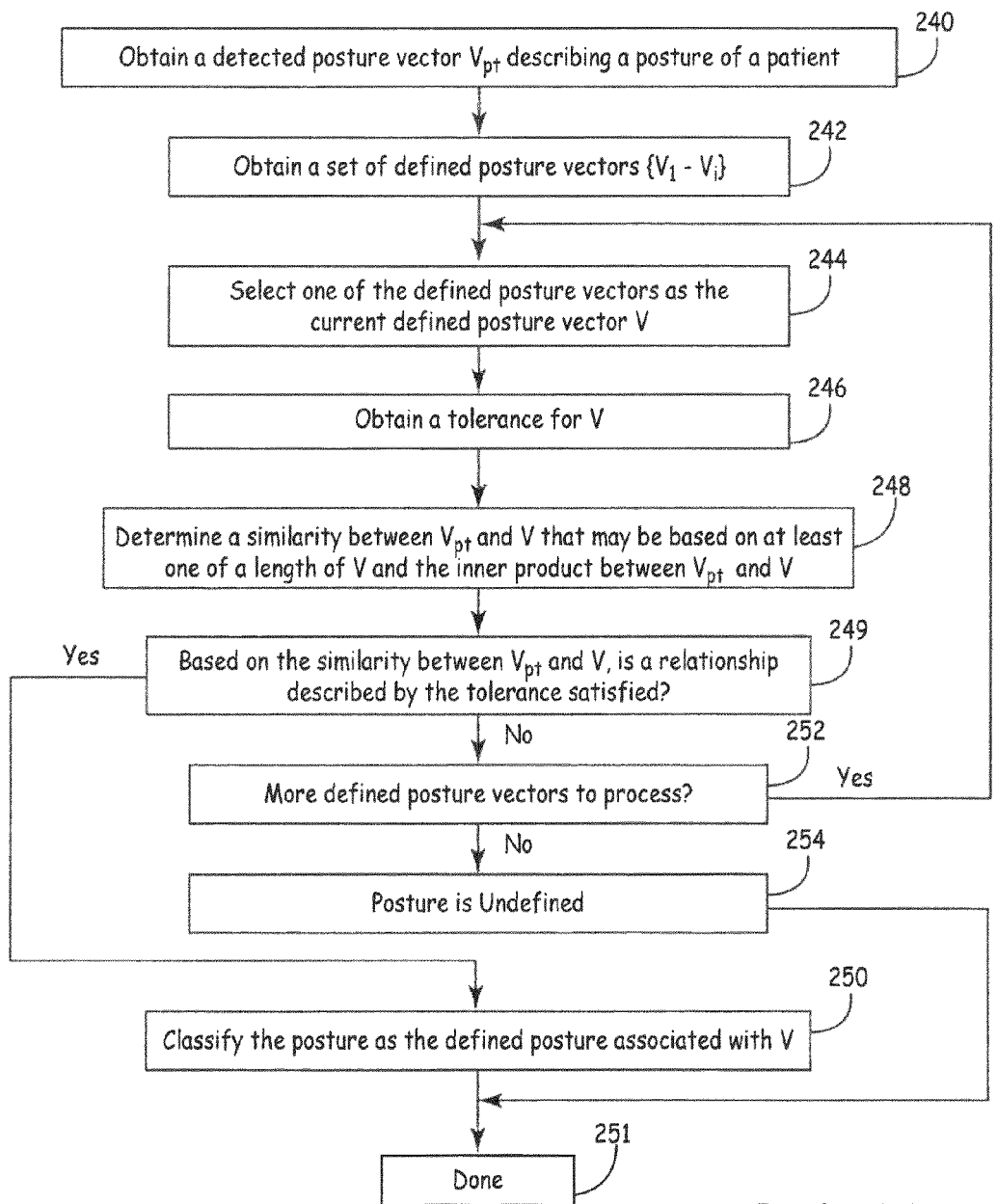
FIG. 14 is a flow diagram of another method of classifying a posture.

FIG. 14 is a flow diagram of another method of classifying a posture according to the current disclosure. This method utilizes some of the processing simplifications discussed above, including the one-time derivation of constant values, Δ, that are derived using squared lengths of defined posture vectors.

According to this method, a detected posture vector $V_{pt}$ is obtained for a posture of a patient (240). Next, a set of defined posture vectors $\{V_1\text{-}V_i\}$ is obtained (242). The defined posture vectors may be any combination of actual and/or virtual defined posture vectors. One of the defined posture vectors is selected from this set for use as the current defined posture vector V (244). A tolerance that is associated with the current defined posture vector V is obtained that is described in terms of a similarity (246). A similarity between $V_{pt}$ and V may then be determined. In one embodiment, the similarity is based on at least one of a length of V, which is a constant, and the inner product between $V_{pt}$ and V (248). Examples of such similarities are discussed above.

Based on the similarity, it is determined whether the relationship specified by the tolerance is satisfied (249). If so, the patient's posture is classified as the defined posture which is associated with defined posture vector V (250), and processing is considered completed (251). Otherwise, if the relationship is not satisfied, and more defined posture vectors are yet to be processed (252), execution returns to step 244, where another defined posture vector is obtained and the process is repeated. If, in step 252, no additional defined posture vectors remain for processing, execution continues to step 254, where the posture is classified as Undefined. Processing is then considered completed (251).

The foregoing method is a general approach that may be used to compare a defined posture vector to a detected posture vector using various techniques described above. Because the determination of the similarity does not require derivation of any angles, posture classification can be completed in a very efficient manner. This process is even further streamlined in one embodiment that utilizes predetermined constants to derive the similarities, thereby reducing processing needed during posture classification.

It may be noted that the steps of FIG. 14 may be utilized in conjunction with other methods such as those shown in FIGS. 12 and 13. For instance, in one embodiment, the steps of FIG. 14 may be used as one way to carry out the functions of steps 220-225 of FIG. 13. Thus, the methods are not to be viewed as mutually exclusive, and many embodiments and combinations of the various method steps are possible.

Figure 15:
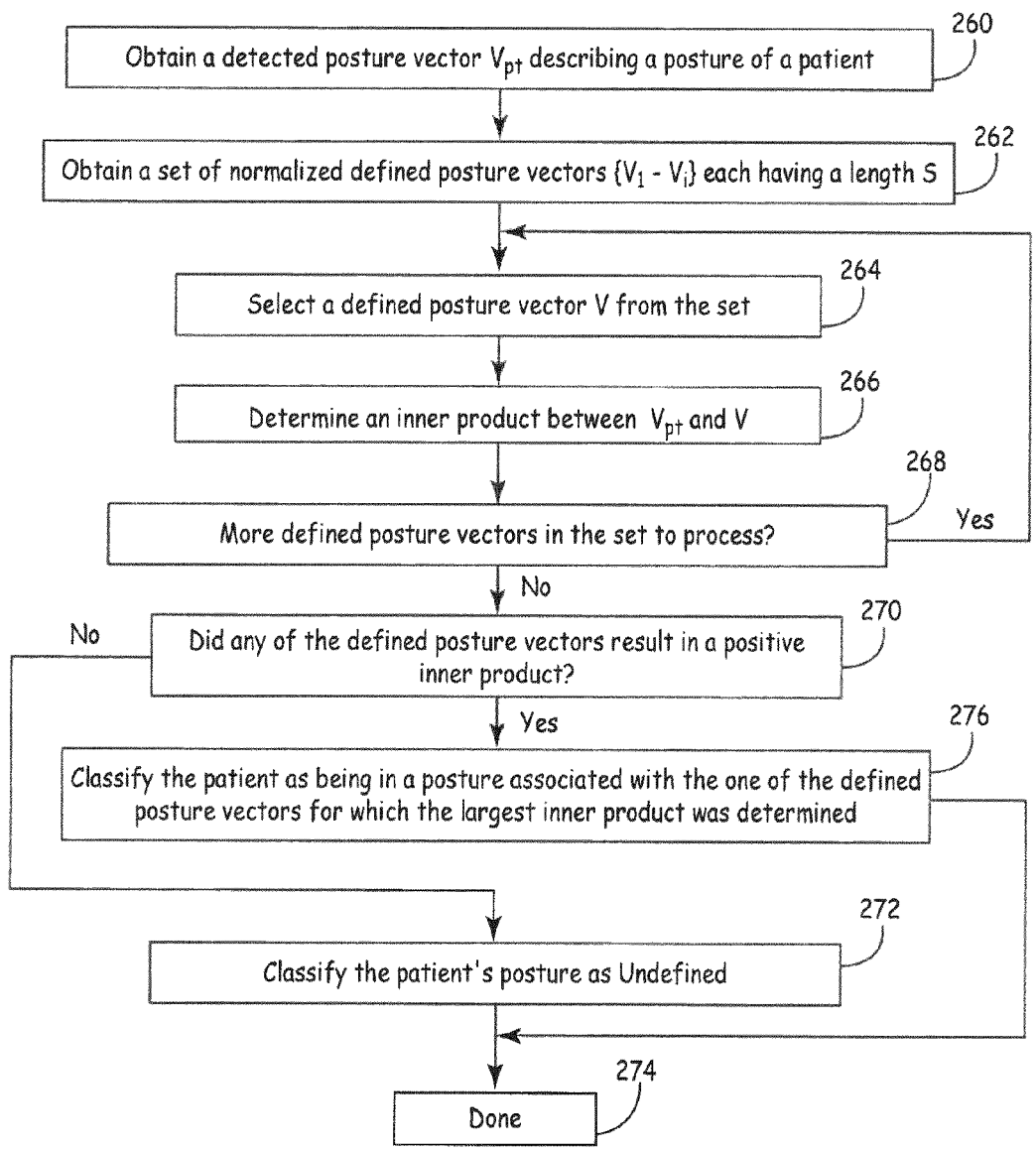
FIG. 15 is a flow diagram of yet another method of classifying a posture.

FIG. 15 is a flow diagram of yet another method of comparing a detected posture vector $V_{pt}$ to defined posture vectors that have been normalized according to one embodiment of the current disclosure. First, a detected posture vector $V_{pt}$ for a posture occupied by a patient is obtained (260). A set of normalized defined posture vectors $\{V_1\text{-}V_i\}$ that each has a length S is obtained for processing (262). The normalized defined posture vectors may be any combination of actual and/or virtual normalized defined posture vectors. A normalized defined posture vector V is then selected from this set (264), and an inner product is derived between this defined posture vector V and $V_{pt}$ (266). If more vectors from the set remain to be processed to obtain an inner product (268), execution returns to step 264, where another one of the defined posture vectors is selected from the first set for processing.

When all of the defined posture vectors from the set have been processed to obtain a respective inner product with $V_{pt}$ (268), it is determined whether any of the defined posture vectors resulted in a positive inner product (270). If not, the patient may be classified in the Undefined posture, since all of the defined posture vectors in the set are in at least a somewhat opposite direction as compared to the detected posture vector (272). Processing is then considered complete (274). If, however, at least one of the defined posture vectors resulted in a positive inner product (270), the patient may be classified as being in whichever posture is associated with the defined posture vector for which the largest positive inner product was obtained (276). Processing is then considered complete (274).

The method of FIG. 15 may be utilized in scenarios such as described in regards to FIG. 9 to classify postures. This method determines the defined posture vector to which the detected posture vector is most similar (or closest). As previously discussed, this type of method is not suited for applications wherein multiple postures are defined in terms of a common defined posture vector (e.g., wherein the Upright, Inverted, Lying Down postures are all defined using the same defined posture vector $V_{Up}$ and discussed in reference to FIG. 8). In these types of embodiments, using the "closest to" relationship will not adequately classify the posture. Therefore, the more generalized approach of FIG. 13 may be employed for posture classification in these implementations.

The method of FIG. 15 is particularly efficient since, depending on the posture definitions, in many cases only a small subset of all defined posture vector will generally produce a positive inner product. In this case, very few processing steps are needed to complete the posture classification. Even when multiple positive inner products are obtained, the processing may be completed using simple comparisons. Thus, this approach combines multiple efficiencies, and is much more efficient than methods that utilize angle derivations or processing intensive functions such as square roots to classify postures.

The method of FIG. 15 may be usefully employed to collect diagnostic information referred to as "posture refinement information" when the patient has been classified in an Undefined posture. Collection of this posture refinement information may be accomplished, for instance, using step 262 of FIG. 15. During this step, the detected posture vector may be compared to all, or some subset of all, of the defined posture vectors in use within the system. This will determine to which defined posture the patient's Undefined posture is considered closest. This information may be recorded to aid in analyzing the patient's posture further and to evaluate system performance in embodiments that utilize this type of Undefined posture classification.

If desired, both of the methods of FIGS. 14 and 15 may be used in combination to classify postures. For instance, in accordance with one embodiment described above, the more general approach of FIG. 14 may be used to determine whether a patient is classified in an Upright, Lying Down, Inverted, or Undefined posture. If in a Lying Down posture, the more specific approach of FIG. 15 may then be used to further classify the posture as being any one of N sub-classifications, which may include Face Up, Face Down, Right Side, Left Side and/or other lying down postures.

Moreover, it may be noted that the process of making an initial posture classification (e.g., Lying Down), and then further classifying a posture based on sub-classifications (Face Up, Face Down, Right Side, Left Side) in the manner described in the foregoing paragraph is not limited to use when the patient is initially classified as Lying Down. For instance, after a patient is classified as being in the Upright posture, further classification could be performed using a set of posture sub-classifications that may including Leaning Forward, Leaning Backward, Leaning Right, Leaning Left. In this manner, once a posture classification is made, a subset of postures for use in further classification may be selected based on the most recent posture classification, with this process being repeated any number of times. If desired, such classification may occur using any combination of the methods of FIGS. 14 and 15.

The above discussion focuses on posture classification, which in one embodiment involves use of DC components of the x, y, and z signals of sensor 40. Similar techniques may be applied to classifying the motion of the patient. A patient's motion may be classified using activity states. In one embodiment, an activity state may be determined from the AC components of the outputs of sensor 40 (as opposed to DC components of the sensor output used to detect posture). For instance, outputs of sensor 40 may be filtered to retain a predetermined frequency range and exclude noise, processed according to various smoothing techniques, and then used to determine motion of a patient. Techniques for processing AC components of sensor 40 to obtain signals indicative of an activity state are described in provisionally-filed commonly-assigned Patent Application Ser. No. 61/080,049 filed Jul. 11, 2008, entitled "Posture State Detection System and Method" referenced above and in commonly-assigned patent application entitled "Posture State Detection Using Selectable System Control Parameters" referenced above.

An activity state definition includes a defined activity parameter value which is similar to a defined posture vector of a posture definition. This defined activity parameter value may specify a level of activity of a patient (e.g., footfalls), or some another value describing motion or lack thereof. As another example of a defined activity parameter value, an activity state may specify a defined activity vector which relates to direction of velocity, direction of acceleration, or some other direction involving motion.

As was the case with posture definitions, an activity state definition may specify a tolerance describing a relationship to the defined activity parameter value. When the defined parameter values involve an activity level, the tolerance may be expressed in terms of a range of scalar values. For instance, processed AC signals of a sensor may provide a range (e.g., 0-100) that indicates a level of activity of a patient. Subsets of this range may be associated with certain activity levels (e.g., 0-20 is associated with an Inactive range, 80-100 is associated with an Active range, etc.). In this case, the tolerance may be expressed using these defined ranges. For instance, the tolerance may be expressed using the range 0-20, which will be compared to a detected activity level of a patient during activity state classification.

The defined activity parameter value may be a defined activity vector indicating a direction of motion rather than a scalar that indicates activity level. When activity state definitions are created that involve vectors, the tolerances may be expressed using relationships similar to those discussed above, and that reference similarities such as those discussed above.

In some embodiments, activity states may be pre-defined within the system, as by device manufacturers. In other cases, activity states may be defined by a user such as a clinician. For instance, a clinician may prompt a patient to begin an activity such as walking on a treadmill. While this is occurring, a clinician may utilize clinician programmer 20 to transmit a command to IMD 12 to cause the patient's activity level to be measured and presented to the clinician via the clinician programmer 20. This reported activity level value may be used to define an activity state of Walking. For instance, this activity state may associated with a selected range of possible activity level values that is determined based on, and that will include, the reported value.

As another example of using patient participation to define an activity state, while the patient is engaging in an activity, one or more vectors indicative of direction of motion of this activity may be obtained from outputs of sensor 40. If desired, the one or more vectors may be processed (e.g., to extract a certain frequency range, filter noise, and/or determine a median or average vector value for instance). The resulting vector may be used with a selected tolerance to create an activity state definition. In this manner, an activity state definition may reference a vector and a tolerance in much the same manner as a posture definition references a defined posture vector and a tolerance.

If desired, some processing of activity vectors may be used to obtain virtual activity vectors. This may occur in any of the ways described above in reference to virtual posture vectors. The virtual activity vectors may then be used to define activity states. Moreover, the activity state definitions may reference a condition, the evaluation of which will result in selection of some aspect of the tolerance. For instance, the condition may determine a size of a cone that surrounds a vector. Thus, any of the techniques described herein for use with posture definitions may be employed for use with activity state definitions.

Once an activity state definition is created, it may be used to classify a patient's activity state. As the patient goes about daily life, the outputs of sensor 40 may be processed to derive a detected activity parameter. This value may be compared to the defined activity parameters contained within the activity state definitions. As was the case with comparison of posture vectors, this comparison may utilize similarities, which may be any of the types of similarities described above. In particular, if the detected activity parameter is a vector, the comparison may be accomplished using any of the techniques described above with respect to the comparison of defined posture vectors and detected posture vectors. Because these techniques do not utilize angle derivations, processing may be performed more efficiently. If the comparison indicates the detected activity parameter satisfies the requirements of a defined activity state, the patient may be classified as being in this state.

Figure 16:
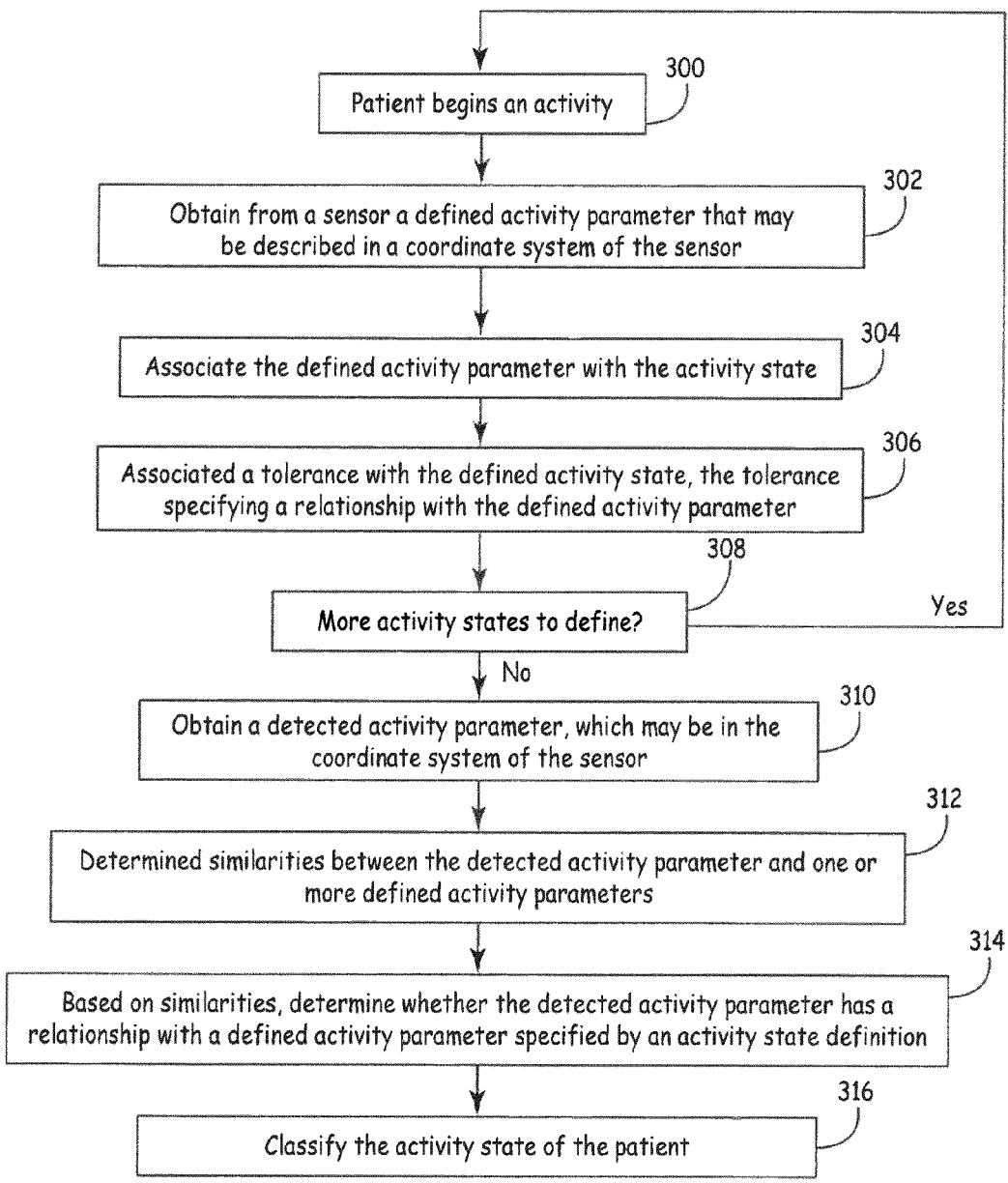
FIG. 16 is a flow diagram of one method of defining and using activity states.

FIG. 16 is a flow diagram describing one method of defining activity states and using the activity state definitions to classify a patient's activity state. This embodiment utilizes patient participation during the definition process, although such participation is not required in other embodiments. A patient is instructed to begin an activity, such as walking on a treadmill (300). A sensor is used to obtain a defined activity parameter (302). In one embodiment, this defined activity parameter may be described in a coordinate system of the sensor without regard to the patient's coordinate system. This defined activity parameter may describe activity level (e.g., footfalls), a vector associated with velocity or acceleration, or some other parameter indicative of movement. The defined activity parameter may be associated with the activity state (304). A tolerance may then be associated with this defined activity state, with the tolerance specifying a relationship with the defined activity parameter (306). Example tolerances are discussed above. If more activity states remain to be defined (308), processing returns to step 300.

After one or more of the desired activity state definitions have been created (308), a detected activity parameter may be obtained from a patient while the patient is going about daily activities (310). In one embodiment, this detected activity parameter may be described in the coordinate system of the sensor without regards to the patient's coordinate system. This is as described above in reference to obtaining posture vectors in the coordinate system of the sensor. This detected activity parameter may indicate a level of activity, a vector indicative of velocity or acceleration, or some other parameter indicative of motion.

Similarities may be determined between the detected activity parameter and one or more defined activity parameters (312). Based on these similarities, it may then be determined whether the detected activity parameter has a relationship with a defined activity parameter as set forth in any of the activity state definitions (314) and the activity state of the patient may be classified (316).

As discussed previously, posture definitions and activity state definitions are each one subset of a more general class of definitions referred to as posture state definitions. A posture state definition references at least one of a defined posture and a defined activity state. Thus, a posture state may involve just a posture, just an activity, or both. Example posture state definitions may include an Upright and Inactive posture state that requires the patient to be in an Upright posture and an Inactive activity state. Another example is an Upright posture state definition which requires the patient to be in an Upright posture without regard to activity state. Yet another example is an Active posture state that just references an Active activity state without regard to posture.

Posture state definitions may be used to classify a patient's posture state. Classification of the patient's posture state may then be used to initiate some action, such as to deliver therapy in a closed-loop manner, diagnose patient conditions, monitor responses to therapy, detect patient falls, issue warnings, initiate storing of data, and/or to initiate other types of actions.

Figure 17:
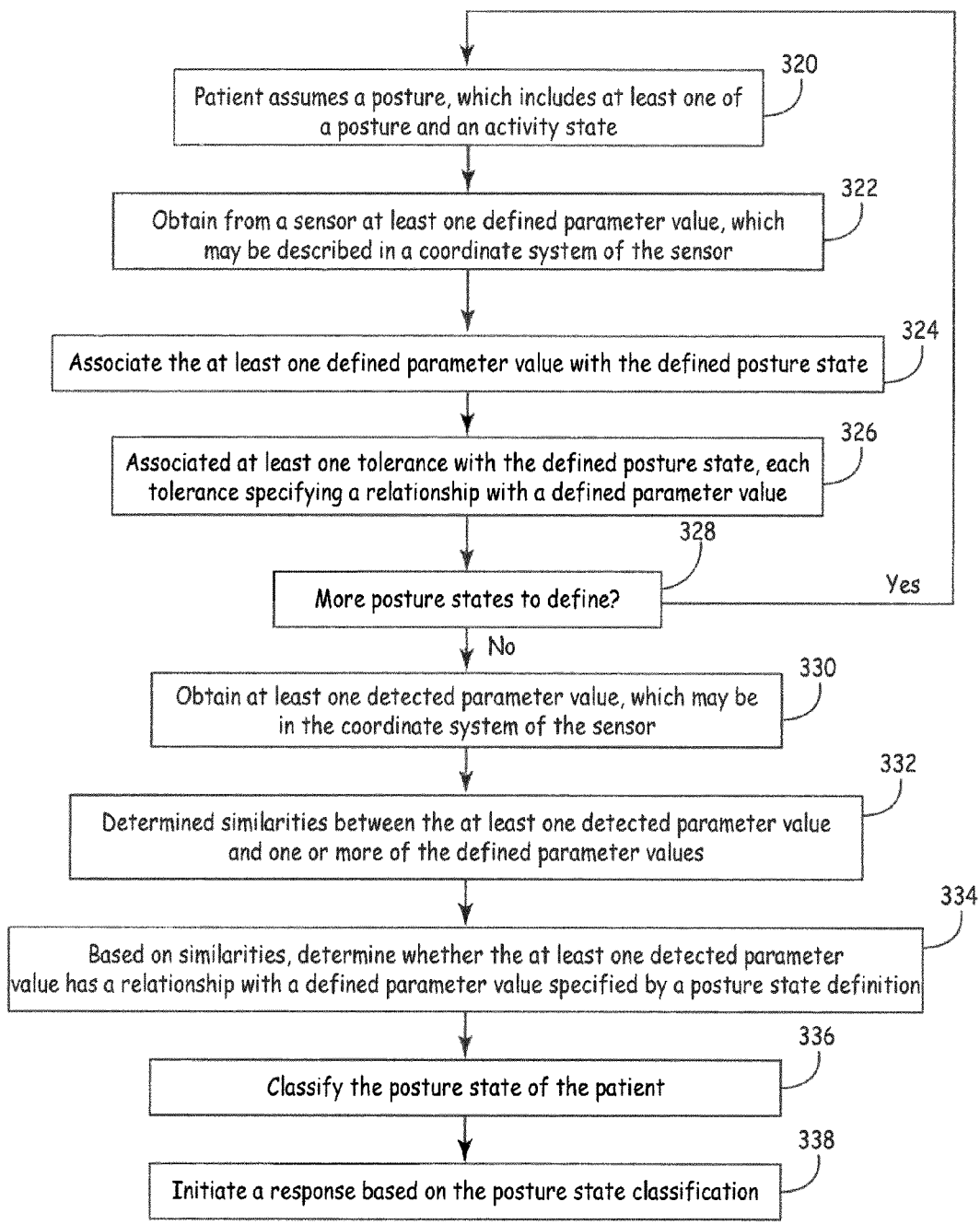
FIG. 17 is a flow diagram of defined and using posture states.

FIG. 17 is a flow diagram illustrating definition and use of posture states according to one embodiment of the disclosure. According this embodiment, definition of the posture state requires patient involvement, although this need not be the case in another embodiment. Therefore, the patient assumes a posture state, which includes at least one of a posture and an activity state (320). At least one value is obtained from the sensor for use as at least one defined parameter value (322). Multiple such values may be obtained if the posture state will involve both a posture and an activity state. The at least one defined parameter value, which may optionally be described in a coordinate system of the sensor, is associated with the defined posture state that was assumed by the patient (324). At least one tolerance may be associated with the defined posture state (326). Multiple such tolerances may be defined if the posture state will involve both a posture and an activity state. Each tolerance specifies a relationship with the defined parameter value (326). If more posture states remain to be defined (328), processing returns to step 320.

When all desired posture states have been defined, at least one detected parameter value may be obtained from the patient (330). This value may be in the coordinate system of the sensor in one embodiment. Similarities may be determined between the at least one detected parameter value and the defined parameter values of the posture state definitions (332). Based on the similarities, a determination is made regarding whether the at least one detected parameter value has relationships with defined parameter values as specified by at least one posture state definition (334). In step 336, the patient's posture state may be classified based on the determination of step 334. That is, if the one or more detected parameter values do have relationships as specified by any one of the posture state definitions, the patient may be classified in this posture state. Otherwise, the patient may be classified in an Undefined posture state, or alternatively remain classified in the defined posture state in which he was last classified in a system that includes hysteresis.

Some response may be initiated based on the posture state classification (338). This may involve initiation, cessation, or modification of therapy delivery. Examples of therapies that may be delivered in a closed-loop manner using techniques presented herein were outlined above, and include electrical stimulation or the delivery of therapeutic agents. Electrical stimulation may be, for example, used to treat patients that suffer from chronic back pain, leg pain, or other pain that cannot be treated through other methods. As a patient changes posture state, which may involve changes in position and/or activity, the stimulation may need to be adjusted in order to maintain efficacy. Such changes in a patient's posture state may be detected, classified, and used to modify a therapy that is currently being delivered, or to select a new therapy for delivery to the patient.

In another embodiment, the detected posture state transition may be used to prompt some notification, or to record some information. For instance, the detected posture state transition may initiate the storing of patient and/or system-related data which may be used to diagnose patient conditions or analyze system operation. Other types of actions may be initiated based on the detected posture state change.

Figure 18:
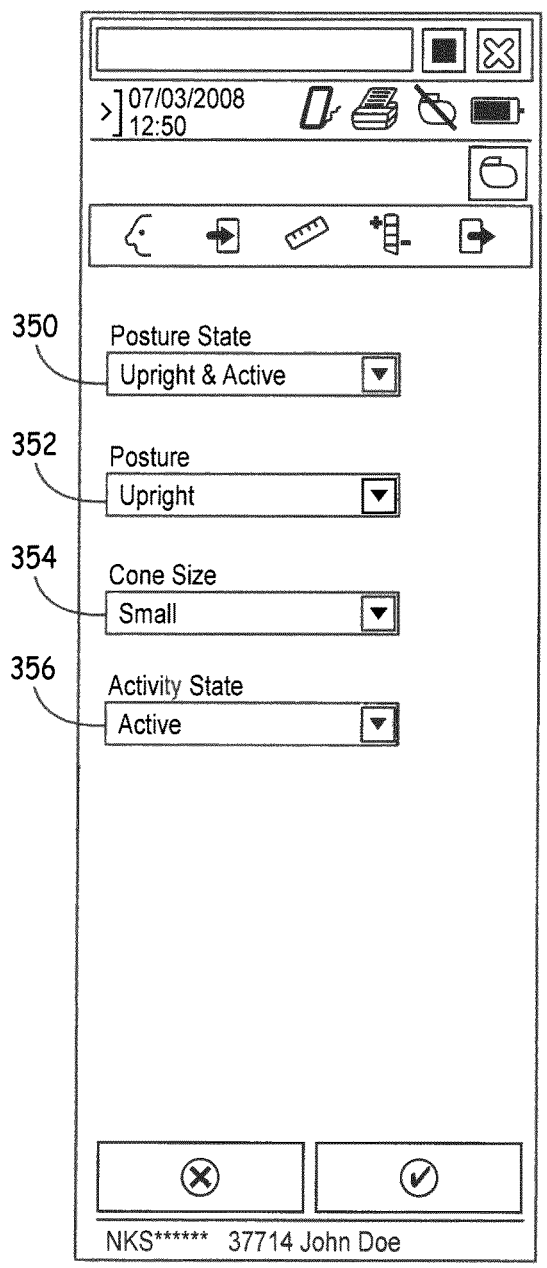
FIG. 18 is a user interface that may be used to define postures, activity states, and posture states according to one embodiment of the current disclosure.

FIG. 18 is a user interface that may be used to define posture states according to one embodiment of the current disclosure. This user interface may be provided on clinician programmer 20 (FIG. 1) for instance. The user interface may include a drop-down menu 350 to select a posture state. The list of available posture states may be pre-populated, if desired. Alternatively, posture state indications may be entered by a patient using some type of key pad or other interface. In the illustration, the posture state Upright and Active has been selected.

A user may employ drop-down menu 352 to select a posture for use in defining the selected posture state. Menu 352 may be populated with available posture definitions, which may be defined by a user by employing patient participation in the manner described above. Techniques for defining and re-defining postures are described in the commonly-assigned Patent Applications entitled "Posture State Classification for a Medical Device" and "Reorientation of Patient Posture States for Posture-Responsive Therapy", both referenced above. In one embodiment, menu 352 includes a No Posture option for use when the posture state is not associated with a posture, but instead is only associated with an activity.

Another drop-down menu 354 is provided to select the tolerance according to the current disclosure. In the current example, the tolerance is expressed that references a similarity value of "Small Cone", which has been pre-associated with a predetermined size (e.g., some pre-selected cosine of an angle, or some other similarity according to any of the approaches discussed above). This type of association may, in one embodiment, be provided by device manufacturers. In another embodiment, this association may be selectable, as by using another screen of the user interface.

The use of drop-down menu 354 may, in one embodiment, override any tolerance that was previously associated with the posture definition. For instance, in such an embodiment, the selection of the Small Cone as shown in FIG. 18 may override a previously-created definition for the Upright posture, which may have included some other cone size, or a region in space other than a cone. In another embodiment, the association of the Upright posture with a tolerance may not occur until menu 354 is employed to select a tolerance.

Another drop-down menu 356 may be used to select an activity state for inclusion in the posture state definition. This menu may be populated with all activity states defined by a user and/or provided by the device manufacturer. In one embodiment, a No Activity selection may be made via menu 356 if the current posture state is not associated with an activity state (e.g., is only associated with a posture).

In one embodiment, another drop-down menu 358 is provided to select the tolerance for the activity state. In the current example, a tolerance of "Large Range" is selected. This tolerance may have been previously associated with some predetermined range of activity level values (e.g., an activity count of 80-100, for example). In an embodiment wherein the activity state involves a vector rather than a scalar value, the selected tolerance must be of a type employed with a vector so that meaningful comparisons may be made during posture state classification. In one embodiment, a check will be employed after selections are made to ensure this is the case.

The example embodiments described herein utilize various efficiencies for performing posture detection and classification, activity state detection and classification, and posture state detection and classification. The efficiencies may include detecting a vector (e.g., a posture vector or activity state vector) in a coordinate system of a sensor without regard to a patient's coordinate system. Such efficiencies may further include classification using non-angle similarities that do not require derivation of angles. Normalization of vectors (e.g., either posture or activity state vectors), as well as use of predetermined constants (e.g. lengths of defined vectors, cosines of pre-selected angles, normalized vector lengths, etc.) also make processing more efficient.

Any of these techniques may be used alone, or in combination with one or more techniques to accomplish posture and activity state detection. Thus, for instance, techniques may be contemplated that utilize a non-angle similarity metric but that do not use the processing efficiencies afforded by classifying posture states using the coordinate system of the sensor. In such an embodiment, sensor 40 may be positioned on the patient in a known orientation, for instance, such that the sensor coordinate system aligns in a known manner with the patient's body coordinate system. In this type of configuration, the defined posture vectors may be selected by a device manufacturer or a user without any participation on the part of the patient. All of the other processing efficiencies described herein may be utilized in that system.

In another embodiment, the processing efficiencies provided by comparing vectors expressed in the coordinate system of the sensor may be utilized while foregoing the use of non-angle similarities. In this case, all of the processing efficiencies described herein except those afforded by eliminating angle derivations may be incorporated into the system. Thus, any one or more of the techniques described herein may be incorporated into a system in a manner that provides superior power conservation and processing efficiency.

In the description above, the various functions, steps, techniques and mechanisms may be performed by processor 34 operating in conjunction with posture state module 41 and/or memory 36 of IMD 12. However, in other examples, data processing and storage may be distributed in a different manner between devices of a therapy system. For example, some of the processing steps to process signals from sensor 40 and classify the posture state of the patient may be performed by a processor of programmer 20 that receives signals from IMD 12 via telemetry communication, for instance. The programmer 20 may then initiate a response based on the posture state classification, and/or may issue a command to IMD 12 to cause the IMD to initiate some response, as will be necessary when the response involves starting, stopping, or modifying therapy being delivered to patient 14 by the IMD 12. In some cases, processor 34 of IMD 12 may perform some processing steps, transmit intermediate information to programmer 20, and the programmer will perform some steps, and re-transfer information to the IMD to complete processing. Many combinations of, and ordering of steps, are possible. In another example, at least some processing may be offloaded from IMD 12 or programmer 20 to a remote device including, e.g., a server that is wireless or otherwise coupled to programmer 20.

In any of the embodiments, posture state definitions 52 may be stored by IMD 12 and/or programmer 20. For instance, both programmer 20 and IMD 12 may store a copy of this information.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to cause one or more processors to support one or more aspects of the functionality described in this disclosure.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that may benefit from the subject matter of this disclosure.

Those skilled in the art will recognize that other modifications may be made to the systems, methods, and techniques described herein. For instance, some of the steps of the methods may be implemented in hardware such as posture state module 41. In many cases, steps may be re-ordered, and some steps may be eliminated. Thus, the description of the embodiments is merely exemplary, with the scope of the invention to be defined by the Claims that follow.

What is claimed is:

1. An implantable medical device, comprising:
   a sensor configured to provide signals indicative of a detected posture vector of a patient;
   a memory configured to store one or more defined posture vectors and to associate each defined posture vector with a tolerance describing a relationship with the defined posture vector; and
   a processor configured to determine, without any derivation of an angle, a respective similarity between the detected posture vector and each of one or more of the defined posture vectors and to classify a posture of the patient based on whether any similarity has a relationship to the respective defined posture vector that is described by the associated tolerance.

2. The device of claim 1, wherein the processor is further configured to determine each similarity based on at least one of an inner product between the detected posture vector and a respective one of the defined posture vectors, a squared length of the detected posture vector, and a squared length of the defined posture vector.

3. The device of claim 1, wherein the processor is configured to determine the defined posture vector to which the detected posture vector is closest.

4. The device of claim 1, wherein the processor is configured to determine each similarity as a distance between the detected vector and a defined vector.

5. The device of claim 4, wherein the processor is further configured to map the distance to obtain a value ranging between a selected minimum value and a selected maximum value, and to use the obtained value to classify the posture of the patient.

6. The device of claim 1, wherein multiple ones of the defined posture vectors are associated with a same posture.

7. The device of claim 6, wherein the multiple ones of the defined posture vectors associated with a same posture describe multiple regions in space interrelated by one or more logical functions.

8. The device of claim 7, wherein at least some of the multiple regions in space overlap with one another.

9. The device of claim 8, wherein the multiple regions in space include one or more toroids and one or more cones.

10. The device of claim 1, wherein the processor is configured to determine each similarity without regard to a coordinate system of the patient.

11. The device of claim 1, wherein the processor is further configured to classify the posture of the patient based on a first set of the one or more defined posture vectors, and to reclassify the posture of the patient based on a second set of the one or more defined posture vectors, each of one or more defined posture vectors in the second set being a sub-classification of a posture in which the patient is first classified.

12. The device of claim 1, wherein the processor is further configured to process multiple ones of the defined posture vectors to obtain a virtual posture vector, and wherein the virtual posture vector is one of the one or more defined posture vectors used to classify the posture of the patient.

13. The device of claim 12, wherein the processor is further configured to determine an average of cross-products of pairs of the multiple ones of the defined posture vectors to obtain the virtual posture vector.

14. The device of claim 12, wherein the processor is further configured to determine a single plane that best approximates planes in which the multiple ones of the defined posture vectors reside, to select multiple vectors that describe the single plane, and to determine a vector that is normal to the single plane for use as the virtual posture vector.

15. The device of claim 12, wherein the processor is further configured to classify the posture of the patient as being Lying Down based on whether the detected posture vector lies outside of a cone surrounding the virtual posture vector and further based on whether the detected posture vector lies within any of one or more cones disposed about one or more of the defined posture vectors associated with the Lying Down posture.

16. The device of claim 1, wherein the processor is further configured to provide signals indicative of an activity state of the patient, and the processor is further configured to classify a posture state of the patient based on whether any similarity has a relationship to the respective defined posture vector that is described by the associated tolerance and further based on the indicated activity state of the patient.

17. The device of claim 1, further comprising a therapy module configured to deliver electrical stimulation therapy to the patient based on the posture classification.

18. A method for use with a medical system having a sensor, comprising:
    obtaining a defined vector indicative of a defined posture state;
    obtaining from the sensor a detected vector that is indicative of a posture state of a patient;
    determining a similarity between the defined vector and the detected vector, the similarity being determined without deriving an angle;
    classifying the posture state of the patient based on the similarity; and
    initiating via the medical system an action related to care provided to the patient, the action being based on the classification of the posture state of the patient.

19. The method of claim 18, wherein classifying the posture state includes classifying the patient as being in at least one of a posture and an activity state.

20. The method of claim 18, wherein the similarity is a cosine of an angle between the defined vector and the detected vector.

21. The method of claim 20, further comprising:
    deriving the cosine of the angle between the defined vector and the detected vector;
    obtaining a tolerance that is associated with the defined vector; and
    if the cosine satisfies a relationship described by the tolerance, classifying the patient as being in the posture state.

22. The method of claim 18, further comprising:
    associating a tolerance with the defined vector; and wherein classifying the posture state comprises determining, based on the similarity, whether the detected vector has a relationship to the defined vector described by the tolerance.

23. The method of claim 22, wherein the tolerance describes a relationship involving at least one of a cone and a toroid disposed about the defined vector.

24. The method of claim 22, wherein the tolerance describes multiple regions in space and wherein classifying the posture state comprises determining, based on the similarity, whether the detected vector lies within one or more of the multiple regions.

25. The method of claim 22, wherein the tolerance interrelates multiple regions in space using one or more logical functions.

26. The method of claim 22, further comprising:
associating the defined vector with a condition; and
wherein classifying the posture state comprises:
evaluating the condition;
selecting a relationship based on the evaluation of the condition; and
determining based on the similarity whether the detected vector has the relationship to the defined vector.

27. The method of claim 18, further comprising:
obtaining multiple defined vectors;
deriving a respective similarity between the detected vector and each of the multiple defined vectors;
determining, based on the similarities, which of the defined vectors is closest to the detected vector; and
classifying the posture state based on the determination.

28. The method of claim 27, wherein determining which of the defined vectors is closest comprises determining with which of the multiple defined vectors the detected vector has a largest inner product.

29. The method of claim 27, wherein deriving the respective similarity comprises obtaining at least one constant value that is based on at least one of a squared length of the defined vector and a cosine of an angle describing a region in space with respect to the defined vector.

30. The method of claim 18, wherein obtaining the defined vector includes obtaining the defined vector from a sensor implanted in the patient while the patient assumes the posture state.

31. The method of claim 30, wherein the defined vector and the detected vector are described in a coordinate system of the sensor and without regard to an orientation of the sensor in relation to the patient.

32. The method of claim 18, further comprising:
obtaining multiple tolerances, each describing a relationship with the defined vector;
evaluating a condition associated with the patient;
selecting one of the multiple tolerances based on the evaluation; and
classifying the posture state based on whether the similarity has a relationship to the defined vector described by the selected tolerance.

33. The method of claim 18, further comprising:
obtaining multiple defined vectors; and
processing the multiple defined vectors to obtain a virtual vector; and
wherein determining the similarity between the defined vector and the detected vector further comprises determining the similarity between the virtual vector and the detected vector.

34. The method of claim 33, wherein processing the multiple defined vectors includes deriving cross-products between pairs of the multiple defined vectors and averaging the cross-products.

35. The method of claim 33, further comprising:
associating multiple regions in space with at least one of the virtual vector and one or more of the multiple defined vectors; and
wherein classifying the posture state of the patient further comprises determining whether the detected vector lies within any of the multiple regions in space.

36. The method of claim 18, wherein the multiple regions in space include at least one toroid and at least one cone.

37. The method of claim 18, wherein the multiple regions in space include a toroid disposed about the virtual vector, and multiple cones, each disposed about a respective one of the multiple defined vectors.

38. The method of claim 18, wherein the similarity is a distance between the detected vector and the defined vector, and wherein classifying the posture state includes mapping the distance to a value that is directionally directly proportional to how similar the defined vector is to the detected vector.

39. The method of claim 18, wherein classifying the posture state of the patient further comprises:
classifying the patient in a first posture state;
obtaining multiple defined vectors associated with the first posture state;
determining a similarity between the detected vector and each of the multiple defined vectors associated with the first posture state; and
re-classifying the posture state of the patient based on the similarities between the detected vector and each of the multiple defined vectors associated with the first posture state.

40. The method of claim 39, wherein the first posture state is a Lying Down posture state and wherein the multiple defined vectors associated with the first posture state are associated with posture states that are sub-classifications of the Lying Down posture state.

41. The method of claim 39, wherein classifying the patient in the first posture state further comprises determining whether the detected vector is in one or more regions in space associated with the defined posture vector, and wherein determining a similarity between the detected vector and each of the multiple defined vectors associated with the first posture state comprises determining to which of the multiple defined vectors the detected vector is closest.

42. The method of claim 18, wherein classifying the posture state of the patient classifies the patient as being in at least one of a posture and an activity state.

43. A medical system, comprising:
a sensor configured to provide a detected vector indicative of a posture state of a patient;
a storage device configured to store one or more defined vectors; and
one or more processors configured to derive a similarity between the detected vector and each of one or more of the one or more defined vectors, wherein deriving the similarity does not require derivation of angles, and to classify the posture state of the patient based on the derived similarities.

44. The medical system of claim 43, further comprising a programmer comprising at least one of the one or more processors.

45. The medical system of claim 43, further comprising a medical device comprising at least one of the one or more processors.

46. The system of claim 43, wherein the processor is one or more processors are further configured to utilize the detected vector to evaluate a condition and to classifying the posture state of the patient based on the evaluation.

47. The system of claim 44, wherein the programmer is configured to allow a user to create one or more posture state definitions that include the one or more defined vectors.

48. The system of claim 43, wherein the sensor is configured to provide each of the defined vectors while the patient is assuming a respectively-associated posture state.

49. The system of claim 48, wherein the defined vectors and the detected vector are each expressed in a coordinate system of the sensor without reference to the coordinate system of the patient, and the one or more processors derive each of the similarities without reference to the coordinate system of the patient.

50. The system of claim 43, wherein the one or more processors are further configured to employ ones of the defined vectors to derive at least one additional defined vector to derive a similarity between the detected vector and the at least one additional defined vector, and to classify the posture state of the patient based on the similarity between the detected vector and the at least one additional defined vector.

51. The system of claim 50, wherein the at least one additional defined vector includes a virtual upright vector, and wherein the one or more processors are further configured to derive a similarity between the detected vector and one of the defined vectors to determine whether to classify the patient as being in an Upright posture state, and to derive a similarity between the detected vector and the virtual upright vector to determine whether to classify the patient as being in a Lying Down posture state.

52. The system of claim 43, wherein each similarity between the detected vector and a defined vector is derived based on at least one of an inner product between the detected vector and the defined vector, a length of the detected vector, and a length of the defined vector.

53. The system of claim 52, wherein each of the defined vectors is normalized to have a same selected length.

54. The system of claim 51, wherein if the patient is classified in the Lying Down posture state, the one or more processors are further configured to derive a similarity between the detected vector and each of ones of the defined vectors associated with the Lying Down posture state to classify the patient in a posture state that is a sub-classification of the Lying Down posture state.

55. The system of claim 46, wherein the evaluation determines at least one of a size and shape of a region in space, and wherein the one or more processors are further configured to classify the posture state of the patient based on a relationship of the detected vector to the region in space as indicated by the derived similarities.

56. The system of claim 43, wherein the detected vector is indicative of acceleration or velocity.

57. The medical system of claim 43, further comprising a response module configured to generate a response based on the posture state classification.

58. The medical system of claim 57, further comprising a storage device, and wherein the response module is configured to generate a response based on the posture state classification comprising storing data in the storage device.

59. The system of claim 57, wherein the response module is a therapy module configured to deliver therapy to the patient based on the posture state classification.

60. The system of claim 57, wherein at least one of the sensor and the response module is implanted within the patient.

61. The system of claim 48, wherein the posture state is which the patient is classified is indicative of posture and activity state.

62. A non-transitory storage medium for storing instructions to cause a processor to:
   obtain a defined vector indicative of a defined posture state;
   obtain from the sensor a detected vector that is indicative of a posture state of a patient;
   determine a similarity between the defined vector and the detected vector, the similarity being determined without deriving an angle;
   classify the posture state of the patient based on the similarity; and
   initiate an action related to at least one of caring for, collecting data describing, and diagnosing, the patient.

* * * * *